United States Patent [19]

Derible et al.

[11] 4,018,922
[45] Apr. 19, 1977

[54] 10-(PIPERIDINO-ALKYL)-PHENOTHIAZINES

[75] Inventors: Pierre Henri Derible, Le Perreux; Jean-Paul Lavaux, Paris, both of France

[73] Assignee: Roussel-UCLAF, Paris, France

[22] Filed: Mar. 25, 1975

[21] Appl. No.: 561,925

Related U.S. Application Data

[60] Division of Ser. No. 497,995, Oct. 19, 1973, Pat. No. 3,891,636, which is a continuation-in-part of Ser. No. 252,461, May 11, 1972, abandoned.

[30] Foreign Application Priority Data

| Nov. 9, 1972 | France | 72.39673 |
| Sept. 3, 1973 | France | 73.31698 |
| May 14, 1971 | France | 71.17509 |
| May 14, 1971 | France | 71.17510 |

[52] U.S. Cl. .......................... 424/247; 260/243 A; 260/293.66; 260/293.82; 260/293.84; 260/293.88; 260/293.9

[51] Int. Cl.² .............. A61K 31/445; A61K 31/54

[58] Field of Search ..... 260/293.9, 293.84, 293.82; 424/247

[56] References Cited

UNITED STATES PATENTS

| 3,126,379 | 3/1964 | Davis | 260/243 A |
| 3,140,284 | 7/1964 | Habicht et al. | 260/243 A |
| 3,193,549 | 7/1965 | Zenitz | 260/243 A |
| 3,305,547 | 2/1967 | Stach et al. | 260/243 A |
| 3,891,636 | 6/1975 | Derible et al. | 260/243 A |

OTHER PUBLICATIONS

Schenker–Herbst, Progress in Drug Research, vol. 5, frontispage and pp. 269, 304 to 307 and 419 to 426, Birkhauser Verlag Basel and Stuttgart (1963).

*Primary Examiner*—John D. Randolph
*Attorney, Agent, or Firm*—Hammond & Littell

[57] ABSTRACT

Novel 10-(piperidino-alkyl)-phenothiazines of the formula

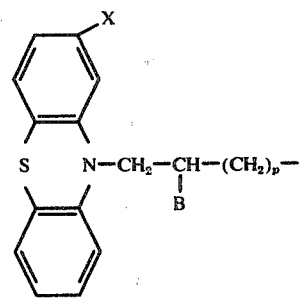

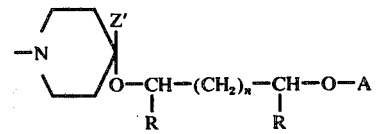

wherein X is selected from the group consisting of hydrogen, chlorine, $-CF_3$, $-OCH_3$ and $SCH_3$, B and R are individually selected from the group consisting of hydrogen and alkyl of 1 to 4 carbon atoms, Z' is selected from the group consisting of hydrogen and alkyl of 1 to 10 carbon atoms, $p$ is 0 or 1, $n$ is 0, 1 or 2 and A is selected from the group consisting of hydrogen, $-COOR_2$ and $-COR_1$, $R_2$ is linear alkyl of 1 to 15 carbon atoms and $R_1$ is selected from the group consisting of alkyl of 1 to 18 carbon atoms optionally containing a double bond or $-O-$ and a polymethoxyphenyl and their non-toxic, pharmaceutically acceptable acid addition salts having neuroleptic, analgesic, spasmolytic and antihistaminic activity and their preparation and novel intermediates.

8 Claims, No Drawings

10-(PIPERIDINO-ALKYL)-PHENOTHIAZINES

PRIOR APPLICATION

This application is a division of our copending, commonly assigned application Ser. No. 497,995 filed Oct. 19, 1973, now U.S. Pat. No. 3,891,636 granted June 24, 1975, which in turn is a continuation-in-part of our copending commonly assigned U.S. patent application Ser. No. 252,461 filed May 11, 1972, now abandoned.

OBJECTS OF THE INVENTION

It is an object of the invention to provide the novel 10-(piperidino-alkyl)-phenothiazines of formula I and their acid addition salts.

It is another object of the invention to provide a novel process for the preparation of the 10-(piperidino-alkyl)-phenothiazines of formula I.

It is a further object of the invention to provide novel intermediates for the compounds of formula I.

It is an additional object of the invention to provide novel therapeutic compositions and to a novel method of treating maniac excitation in warm-blooded animals.

These and other objects and advantages of the invention will become obvious from the following detailed description.

THE INVENTION

The novel products of the invention are selected from the group consisting of 10-(piperidino-alkyl)-phenothiazines of the formula

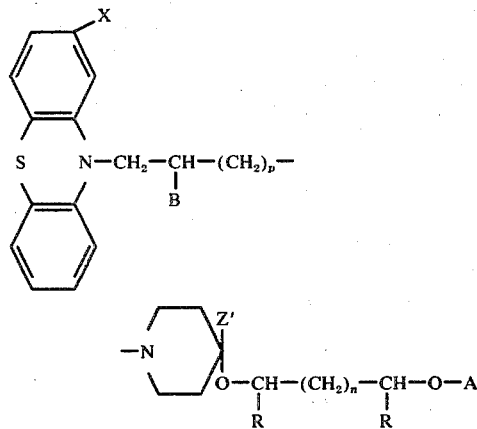

wherein X is selected from the group consisting of hydrogen, chlorine, —$CF_3$, —$OCH_3$ and —$SCH_3$, B and R are individually selected from the group consisting of hydrogen and alkyl of 1 to 4 carbon atoms, Z' is selected from the group consisting of hydrogen and alkyl of 1 to 10 carbon atoms, $p$ is 0 or 1, $n$ is 0, 1 or 2 and A is selected from the group consisting of hydorgen, —$COOR_2$ and —$COR_1$, $R_2$ is linear alkyl of 1 to 15 carbon atoms and $R_1$ is selected from the group consisting of alkyl of 1 to 18 carbon atoms optionally containing a double bond or —O— and a polymethoxyphenyl and their non-toxic, pharmaceutically acceptable acid addition salts.

Examples of suitable acids for the formation of the non-toxic, pharmaceutically acceptable acid addition salts are mineral acids such as hydrochloric acid, hydrobromic acid, hydroiodic acid, nitric acid, sulfuric acid or phosphoric acid or an organic acid such as acetic acid, maleic acid, fumaric acid, succinic acid, tartaric acid, citric acid, oxalic acid, alkane sulfonic acid or arylsulfonic acid.

The novel process of the invention for the preparation of a compound of formula I comprises reacting a compound of the formula

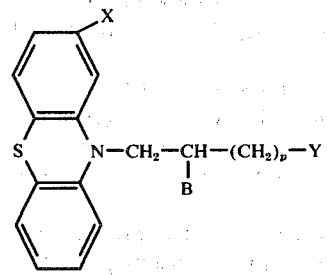

wherein X, B and $p$ have the above definitions and Y is chlorine or bromine with a piperidine of the formula

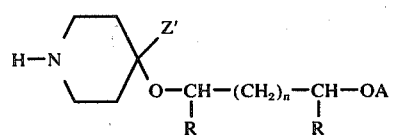

wherein Z', R, $n$ and A have the above definitions to form the corresponding compound of formula I which may be reacted with an organic or mineral acid to form the acid addition salt.

When A is hydrogen, the resulting product may be further reacted with an acid chloride of the formula

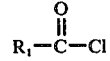

to form the product of formula I wherein A is

or with an alkyl chloroformate of the formula

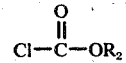

to obtain a compound of formula I wherein A is

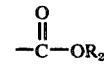

and the corresponding acid addition salts thereof may be formed in the usual manner.

In a preferred mode of the process, the compound of formula II is dissolved in an inert organic solvent containing an equimolar amount of an organic base to act as an acid acceptor such as triethylamine and is then reacted with an equimolar amount of the compound of formula III. If Y is chlorine, it is preferred to operate in the presence of an equimolar amount of sodium iodide at a temperature between room temperature and reflux for 10 to 100 hours. When the reaction is complete, the triethylamine salt may be filtered off and the product of formula I may be recovered from the filtrate.

The reaction of the compound of formula I when A is hydrogen with an acid chloride or a lower alkyl chloroformate is preferably effected at room temperature in an organic solvent such as benzene in the presence of an organic base such as triethylamine to form the hydrochloride.

The acid addition salts may be prepared by reacting the free base of formula I with an acid, preferably in an organic solvent such as anhydrous benzene, ethyl ether, ethanol or acetone. The free base need not be isolated before the reaction.

The piperidine compounds of formula III are novel products and may be formed by reacting a cyclic acetal of 1-benzyl-4-piperidone of the formula

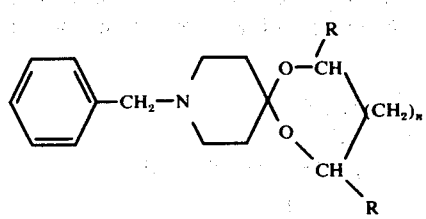

IV with lithium aluminum hydride in the presence of a Lewis acid such as aluminum chloride or zinc chloride or an organo magnesium compound of the formula

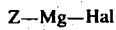 V wherein Hal is chlorine, bromine or iodine and Z is alkyl of 1 to 10 carbon atoms to obtain the corresponding compound of the formula

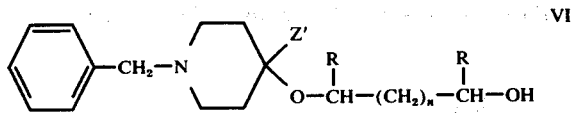 VI wherein R, Z' and n have the above definition, reacting the latter with hydrogen in the presence of a palladium catalyst to form the corresponding compound of formula III.

In a modification of the said process, the compound of formula VI may be reacted with an acid chloride of the formula

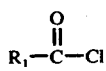

or an alkyl chloroformate of the formula

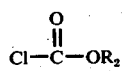

and reacting the reaction product with hydrogen in the presence of a palladium catalyst to form the corresponding compound of formula III wherein A is

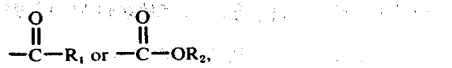

respectively.

In a preferred embodiment of the process, the cyclic acetal of formula IV is added to a lithium aluminum hydridealuminum chloride mixture suspended in anhydrous ether and the mixture is allowed to stand for 1 to 5 hours at a temperature of 15° C to reflux, hydrolyzing the formed complex with water and making the mixture alkaline with sodium hydroxide and recovering the compound of formula VI by conventional means such as extraction followed by distillation.

In another embodiment, the organo-magnesium compound of formula V is formed by reacting an alkyl bromide with magnesium in a solvent such as anhydrous ether in the presence of iodine and the compound of formula IV in an anhydrous solvent such as benzene is added thereto. The first solvent is then removed by distillation and the mixture is refluxed for 10 to 24 hours, cooled and hydrolyzed with a saturated aqueous solution of ammonium chloride. Again, the compound of formula VI may be recovered by standard procedures.

The hydrogenation of the compound of formula VI or the ester thereof with an alkane carboxylic acid is preferably effected by suspending the products in absolute ethanol and stirring the suspension in a hydrogen atmosphere in the presence of 1 to 10% of pallidized charcoal. The hydrogen pressure is between atmospheric pressure and 10 kg/cm$^2$ at a temperature of 30 to 70° C. After absorption of the theoretical amount of hydrogen, the catalyst is filtered from the organic phase and the product is recovered by conventional means such as distillation of the ethanol and further distillation of the residue.

The reaction of the product of formula VI with the acid chloride is effected by dropwise addition of the acid chloride to a solution of the product of formula VI and triethylamine in benzene with ice cooling and after standing for 24 to 48 hours at room temperature, the precipitate formed is removed by filtration. The filtrate is washed first with aqueous sodium bicarbonate, and then with water, the solvent evaporated and the residue is distilled.

Also novel products of the invention are 1-benzyl-4-piper-idyloxy-alkanols of the formula

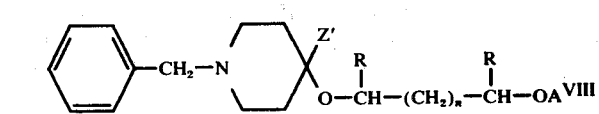

wherein A, n, Z' and R have the above definitions.

The cyclic acetals of formula IV may be prepared by reacting a diol of the formula

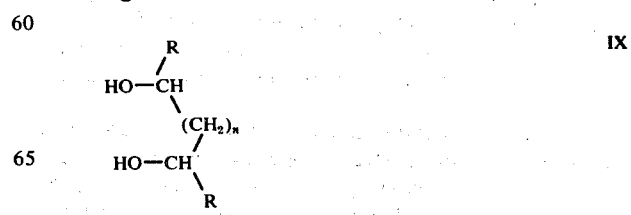 IX wherein R and n have the above definitions with 1-benzyl-4-piperidone in the presence of hydrochloric acid by known processes.

The piperidine compounds of formula III are useful novel intermediates for the present process for the preparation of the therapeutically active compounds of formula I.

The novel therapeutic compositions are comprised of an effective amount of a compound of formula I or its non-toxic, pharmaceutically acceptable acid addition salt and a pharmaceutical carrier. The compositions may be in the form of injectable solutions or suspensions in ampoules or multiple dose flacons or in the form of tablets, coated tablets, gelules, granules, suppositories, pomades, creams and gels prepared in the usual fashion. The usual daily oral dose may be 10 mg to 1 mg.

Examples of suitable carriers are excipients usually used in pharmaceuticals such as talc, arabic gum, lactose, starch, magnesium stearate, cocoa butter, aqueous or non-aqueous media, animal or vegetable fats, paraffin derivatives, glycols, wetting agents, dispersing agents, emulsifiers or preservatives.

The compositions are useful in the treatment of neurovegetative imbalance and character disorders, such as maniac excitation, behavior troubles, various allergic manifestations, pain and spasmodic trouble in the digestive tract.

For example, 10-[3-(4-[2-hydroxy-ethoxypiperidino)-propyl]-phenothiazine hydrochloride has particularly remarkable antihistaminic properties as seen by its antagonism to histamine on the isolated ileum of guinea pigs at a dose of $5 \times 10^{-10}$ gm/liter. Also, 10-[3-[4-(2-hydroxyethoxy)-4-methylpiperidino]-propyl]-2-trifluoromethyl-phenothiazine hydrochloride has excellent neuroleptic activity as can be seen by the traction test wherein the $ED_{50}$ of the product, dose which prevents 50% of the animals to reestablish themselves in 5 seconds, is 0.85 mg/kg when administered intraperitoneally.

The novel method of the invention for treating maniac excitation in warm-blooded animals comprises administering to warm-blooded animals an effective amount of a compound of formula I or its non-toxic, pharmaceutically acceptable acid addition salts. The products may be administered orally, transcutaneously or rectally. The usual daily dose in humans is 0,17 to 17 mg/kg depending on the method administration and the product.

In the following examples there are described several preferred embodiments to illustrate the invention. However, it should be understood that the invention is not intended to be limited to the specific embodiments.

EXAMPLE I

PREPARATION OF 2-(4-PIPERIDYLOXY)-ETHANOL

STEP A: 8-benzyl-1,4-dioxa-8-aza-spiro[4,5]-decane 68.3 g (1.1 mole) of ethylene glycol and 1 liter of anhydrous benzene were added to a 2 liter, 3-neck flash equipped with a gas inlet and a Dean Stark separator and the mixture was refluxed to remove any possible water present. Then, 189 gm (1 mole) of 1-benzyl-4-piperidone were added and reflux was continued while bubbling dry gaseous hydrogen chloride therethrough until 18 ml (1mole) of water was collected (about 6 hours). After cooling, the precipitate formed was recovered by vacuum filtration, was washed with benzene and crystallized from absolute ethanol to obtain 213 g (79% yield) of 8-benzyl-1,4-dioxa-8-aza-spiro[4,5]decane hydrochloride in the form of white crystals melting at 262° C.

The said product was suspended in 1 liter of anhydrous ether and a stream of ammonia was bubbled therethrough for 4 hours. The solid residue was filtered off and the ether filtrate was evaporated to dryness to obtain 178 g (76% yield based on 1-benzyl-4-piperidone) of 8-benzyl-1,4-dioxa-8-aza-spiro [4,5] decane in the form of a clear amber oil which crystallized upon refrigeration. It melted at <50° C.

Analysis: $C_{14}H_{19}NO_2$; Calculated: %N, 6.0; Found: %N, 6.0.

STEP B: 2-[1-benzyl-4-piperidyloxy]-ethanol 106.8 g of (0.8 mole) of aluminum chloride were added to a 2 liter, 3-neck flask and then 800 ml of anhydrous ether were added thereto with strong cooling. The mixture was stirred for 30 minutes and then a suspension of 7.6 g (0.2 mole) of lithium aluminum hydride in 200 ml of ether was added thereto. The mixture was stirred for 30 minutes and then a solution of 93.2 g (0.4 mole) of 8-benzyl-1,4-dioxa-8-aza-spiro [4,5] decane in 400 ml of anhydrous ether was added thereto dropwise. After the addition, stirring was continued at room temperature for 2 hours and 1 liter of water was then slowly added with strong cooling. The mixture was made alkaline with 90 g of sodium hydroxide pellets and the ether phase was decanted off. The aqueous layer was extracted again with ether and the combined ether phases were dried and the ether removed by distillation. The residue was distilled to obtain 63 g (67% yield) of 2-[1-benzyl-4-piperidyloxy]-ethanol in the form of a clear oil boiling at 140° C at 0.1 mm Hg and having a refractive index $n_D^{20} = 1.633$.

Analysis: $C_{14}H_{21}NO_2$; Calculated: %N, 6.0; Found: %N, 5.9.

STEP C: 2-(4-piperidyloxy)-ethanol

Hydrogen was reacted with a solution of 48 g (0.204 mole) of 2-[1-benzyl-4-piperidyloxy]-ethanol in 500 ml of absolute ethanol at 50° C in the presence of 5 g of 5% palladized charcoal until the theoretical amount of hydrogen was absorbed. The catalyst was filtered off and the ethanol was evaporated from the filtrate. The residue was distilled to obtain 22 g (74% yield) of 2-(4-piperidyloxy)-ethanol as a colorless oil which crystallized on cooling. The oil boiled at 110° C at 0.01 mm Hg and after crystallization from cyclohexane, the product melted at 72° C.

Analysis: $C_7H_{15}NO_2$; Calculated: %C, 57.9; %H, 10.4; %N, 9.7; Found %C, 57.5 %H, 10.5; %N 9.8.

EXAMPLE II

PREPARATION OF 3-(4-piperidylozy)-propanol

Using the procedure of Step A of Example I, 83.6 g (1.1 mole) of propanediol-1,3 were reacted to form 180 g (73% yield based on 1-benzyl-4-piperidone) of 9-benzyl-1,5-dioxa-9-aza-spiro [5,5] undecane as a clear amber oil which crystallized on cooling (M.P. <50° C).

Analaysis: $C_{15}H_{21}NO_2$; Calculated: %N, 5.7; Found: %N, 5.6.

Using the procedure of Step B of Example I, 98.8 g (0.4 mole) of 9-benzyl-1,5-dioxa-9-aza-spiro [5,5] undecane were reacted to form 48g (48% yield) of 3-(1-benzyl-4-piperidyloxy)-propanol as a clear oil boiling at 160° C at 0.1 mm Hg and a refractive index $n_D^{20}$ = 1.531.

Analysis: $C_{15}H_{23}NO_2$; Calculated: %N, 5.6; Found: %N, 5.7.

Using the procedure of Step C of Example I, 47.5 g (0.19 mole) of 3-(1-benzyl-4-piperidyloxy)-propanol were reacted to obtain 22.2 g (73% yield) of 3-(4-piperidyloxy)-propanol as a colorless oil boiling at 112° C at 0.01 mm Hg and having a refractive index $n_D^{20}$ = 1.488.

Analysis: $C_8H_{17}NO_2$; Calculated: %C, 60.3; %H, 10.8; %N, 8.8; Found: %C, 60.4; %H, 10.7; %N, 9.0.

EXAMPLE III

PREPARATION OF 2-(4-PIPERIDYLOXY)-1,2-DIMETHYL-ETHANOL

Using the procedure of Step A of Example I, 99.1 g (1.1 mole) of butylene glycol were reacted to obtain 200 g (77% yield based on 1-benzyl-4-piperidone) of 8-benzyl-1,4-dioxa-2,3-dimethyl-8-aza-spiro [4,5] decane as a clear oil.

Analysis: $C_{16}H_{23}NO_2$; Calculated: %N, 5.4; Found: %N, 5.6.

Using the procedure of Step B of Example I, 130.6 g (0.5 mole) of 8-benzyl-1,4-dioxa-2,3-dimethyl-8-aza-spiro [4,5] decane were reacted to form 83.3 g (63%) of 2-(1-benzyl-4-piperidyloxy)-1,2-dimethyl-ethanol as a clear oil boiling at 150-155° C at 0.01 mm Hg and having a refractive index $n_D^{20}$ 1.521.

Analysis: $C_{16}H_{25}NO_2$; Calculated: %N, 5.3; Found: %N, 5.5.

Using the procedure of Step C of Example I, 83.3 g (0.315 mole) of 2-(1-benzyl-4-piperidyloxy)-1,2-dimethyl-ethanol were reacted to form 37.5 g (75% yield) of 2-(4-piper-idyloxy)-1,2-dimethyl-ethanol which after crystallization from cyclohexane occurred as white crystals melting at 88° C.

Analysis: $C_9H_{19}NO_2$; Caluclated: %C, 62.4; %H, 11.1, %N, 8.1; Found: %C, 62.2; %H, 10.9, %N, 8.0.

EXAMPLE IV

PREPARATION OF 4-(4-PIPERIDYLOXY)-BUTANOL form

Using the procedure of Step A of Example I, 57.6 g (0.64 mole) of 1,4-butanediol were reacted to obtain 139.6 g (92% yield based on 1-benzyl-4-piperidone) of 10-benzyl-1,6-dioxa-10-aza-spiro [5,6] dodecane in the form of a clear oil which crystallized on cooling and had an instaneous melting point of 52° C.

Analysis: $C_{16}H_{23}NO_2$; Calculated: %N, 5.4; Found: %N, 5.2.

Using the procedure of Step B of Example I, 110 g (0.421 mole) of 10-benzyl-1,6-dioxa-10-aza-spiro [5,6] dodecane were reacted to obtain 71.5 g (65% yield) of 4-(1-benzyl-4-piperidyloxy)-butanol as a clear oil boiling at 165° C at 0.05 mm Hg.

Analysis: $C_{16}H_{25}NO_2$; Calculated: %N, 5.3; Found: %N, 5.6.

Using the procedure of Step C of Example I, 82.9 g (0.314 mole) of 4-(1-benzyl-4-piperidyloxy)-butanol were reacted to obtain 34.1 g (61% yield) of 4-(4-piperidyloxy)-butanol as a colorless oil boiling at 120° C at 0.05 mm Hg and having a refractive index $n_d^{22}$ = 1.486.

Analysis: $C_9H_{19}NO_2$; Calculated: %C, 62.4; %H, 11.1; %N, 8.1; Found: %C, 61.9; %H, 11.2; %N, 8.0.

EXAMPLE V

PREPARATION OF ETHYL 2-(4-PIPERIDYLOXY)-ACETATE

STEP A: ETHYL 2-([1-BENZYL-4-PIPERIDYLOXY])-ACETATE 15.6 g (0.2 mole) of acetyl chloride were added dropwise while cooling at 20° C with an ice bath to a solution of 47 g (0.2 mole) of 2-(1-benzyl-4-piperidyloxy)-ethanol, prepared according to the step B of Example I, and 20.2 g (0.2 mole) of triethylamine in 300 ml of benzene and after standing for 48 hours at room temperature, the precipitate was removed by vacuum filtration. The benzene filtrate was washed with aqueous sodium bicarbonate solution, then water, dried and the benzene distilled off. The residue was distilled to obtain 36.5 g (66% yield) of ethyl 2-(1-benzyl-4-piperidyloxy)-acetate as a clear oil boiling at 160°–170° C at 0.1 mm Hg and having a refractive index $n_D^{20}$ = 1.512.

Analysis: $C_{16}H_{23}NO_3$; Caluclated: %C, 69.3; %H, 8.4; %N 5.1; Found: %C, 68.7; %H, 8.4; %N, 4.9.

STEP B: ETHYL 2-(4-PIPERIDYLOXY)-ACETATE

A solution of 36.4 g (0.131 mole) of ethyl 2-(1-benzyl-4-piperidyloxy)-acetate in 200 ml of absolute ethanol was reacted with hydrogen at 50° C in the presence of 3.5 g of 5% palladized charcoal until the theoretical amount of hydrogen was absorbed and the catalyst was filtered off. The ethanol was evaporated off and the residue was distilled to obtain 18.2 g (74% yield) of ethyl 2-(4-piperidyloxy)-acetate as a clear oil boiling at 102° C at 0.1 mm Hg and having a refractive index $n_D^{20}$ = 1.4665.

Analysis: $C_9H_{17}NO_3$; Calculated: %C, 57.7; %H, 9.2; %N, 7.5; Found: %C, 57.5; %H, 9.2; %N, 7.5.

EXAMPLE VI

ETHYL 2-(4-PIPERIDYLOXY)-OCTANOATE 32.4 g (0.2 mole) of octanoyl chloride were added dropwise at 20° C (cooling with an ice bath) to a solution of 47 g (0.2 mole) of 2-(1-benzyl-4-piperidyloxy)-ethanol and 20.2 g (0.2 mole) of triethylamine in 300 ml of benzene and after standing for 24 hours at room temperature, the precipitate was removed by vacuum filtration. The benzene filtrate was washed with aqueous sodium bicarbonate solution, then with water, dried and the benzene evaporated off. The residue was dissolved in 300 ml of absolute ethanol and the solution was reacted with hydrogen at 50° C in the presence of 4.5 g of 5% palladized charcoal until the theoretical amount of hydrogen was absorbed. The catalyst was filtered off and after evaporation of the ethanol, the residue was distilled to obtain 35.5 g (64% yield) of ethyl 2-(4-piperidyloxy)-octanoate as a clear oil boiling at 150°–156° C at 0.1 mm Hg and having a refractive index $n_d^{20}$ = 1.464.

Analysis: $C_{15}H_{29}NO_3$; Calculated: %C, 66.4; %H, 10.8; %N, 5.2; Found: %C, 66.0; %H, 10.7; %N, 5.3.

EXAMPLE VII

PREPARATION OF 2-(4-METHYL-4-PIPERIDYLOXY)-ETHANOL

STEP A: 2(1-BENZYL-4-METHYL-4PIPERIDYLOXY)-ETHANOL 40 g of methyl bromide were absorbed in 150 ml of ether cooled to −10° C in a flask and then 9.6 g of magnesium turnings, 50 ml of ether and a crystal of iodine were added to a second flask. The methyl bromide solution was then added dropwise to the second flask followed by the addition of a solution of 46.6 g of 8-benzyl-1,4-dioxa-8-aza-spiro [4,5] decane in a liter of anhydrous benzene. The ether was then evaporated off and the mixture was refluxed for 16 hours. The mixture was cooled and hydrolyzed with a saturated ammonium chloride aqueous solution. The benzene phase was decanted and the aqueous phase was extracted with ether. The organic phase was dried over sodium sulfate and evaporated to dryness in vacuo. The residue was distilled under reduced pressure to obtain 42.8 g of 2-(1-benzyl-4-methyl-4-piperidyloxy)-ethanol as a colorless oil boiling at 136°—140° C at 0.1 mm Hg and having a refractive index $n_D^{26} = 1.527$.

Analysis: $C_{15}H_{23}NO_2$; molecular weight = 249.3; Calculated: %C, 72.25; %H, 9.30; %N, 5.62; Found: %C, 72.4; %H, 9.2; %N, 5.9.

STEP B: 2-(4-METHYL-4-PIPERIDYLOXY)-ETHANOL

A solution of 51.5 g of 2-(1-benzyl-4-methyl-4-piperidyloxy)-ethanol in 500 ml of absolute ethanol was reacted with hydrogen at 50° C in the presence of 5 g of 5% palladized charcoal until the theoretical amount of hydrogen was absorbed (about 3½ hours) and the catalyst was then filtered off. The ethanol was evaporated and the residue was distilled under reduced pressure to obtain 24 g of 2-(4-methyl-4-piperidyloxy)-ethanol as a colorless oil boiling at 80°–86° C at 0.01 mm Hg and having a refractive index $n_D^{24} = 1.481$.

Analysis: $C_8H_{17}NO_2$; molecular weight = 159.2; Calculated: %C 60.34; %H, 10.76; Found: % 56.9; %, 10.5.

EXAMPLE VIII

PREPARATION OF 2-(4-ETHYL-4-PIPERIDYLOXY)-ETHANOL

STEP A: 2-(1-BENZYL-4-ETHYL-4-PIPERIDYLOXY)-ETHANOL 87.5 g of ethyl bromide dissolved in 100 ml of ether were added dropwise over 30 minutes to 19.2 g of magnesium in 100 ml of ether refluxing in a flask and the resulting solution was cooled. A solution of 46.6 g of 8-benzyl-1,4-dioxa-8-aza-spiro [4,5] decane in 250 ml of benzene was added thereto and the ether was evaporated off. 250 ml. of benzene were added and the mixture was refluxed for 20 hours. The mixture was cooled and hydrolyzed with a saturated aqueous ammonium chloride solution. The benzene phase was decanted and the aqueous phase was extracted with methylene chloride. The methylene chloride phase was washed with water until neutral, dried over sodium sulfate and the solvent was distilled off under reduced pressure. The residue was distilled to obtain 37.6 g of 2-(1-benzyl-4-ethyl-4-piperidyloxy)-ethanol as a colorless oil boiling at 152°–156° C at 0.5 mm Hg which was used as is for the next step.

STEP B: 2-(4-ETHYL-4-PIPERIDYLOXY)-ETHANOL

A solution of 37 g of 2-(1-benzyl-4-ethyl-4-piperidyloxy)-ethanol in 300 ml of absolute ethanol was reacted with hydrogen at 50° C in the presence of 4 g of 10% palladized charcoal until the theoretical amount of hydrogen was absorbed (about 3 hours) and the catalyst was filtered off. The ethanol was evaporated off and the residue was distilled to obtain 19.2 g of 2-(4-ethyl-4-piperidyloxy)-ethanol as a colorless oil boiling at 102°–106° C at 0.5 mm Hg.

Analysis: $C_9H_{19}NO_2$; molecular weight = 173.26; Calculated: %C 62.39; %H, 11.05; %N, 8.08; Found; %C, 62.4; %H, 10.8; %N, 8.0.

EXAMPLE IX

PREPARATION OF 2-(4-PROPYL-4-PIPERIDYLOXY)-ETHANOL

Step A: 2-(1-benzyl-4-propyl-4-piperidyloxy)-ethanol and hydrochloride

A solution of 108 g of propyl bromide in 250 ml of ether was added dropwise to a refluxing mixture of 19.2 g of magnesium in 100 ml of ether and then a solution of 46.6 g of 8-benzyl-1,4-dioxa-8-aza-spiro [4,5] decane in 500 ml of benzene was added in increments. The ether was evaporated off and then cooled and hydrolyzed with a saturated aqueous ammonium chloride solution. The benzene phase was decanted and the aqueous phase was extracted with ether. The ether phase was washed with water until neutral, dried over sodium sulfate and the solvents removed under reduced pressure. The residue (B.p. = 129° C at 0.1mm/Hg) was rectified to obtain 28 g of 2-(1-benzyl-4-propyl-4-piperidyloxy)-ethanol as a yellowish oil. The product was dissolved in 250 ml of ether and 13 ml of a 5N hydrogen chloride solution in ether were added thereto. The product was vacuum filtered and crystallized from isopropanol and dried in vacuo to obtain 12.9 g of 2-(1-benzyl-4-propyl-4-piperidyloxy)-ethanol hydrochloride in the form of colorless crystals melting at 196° C.

Analysis: $C_{17}H_{28}ClNO_2$; molecular weight = 313.87; Calculated: %C, 65.06; %H, 8.99; %Cl, 11.30; %N, 4.46; Found: %C, 65.1; %H, 8.9; %Cl, 11.6; %N, 4.1.

STEP B: 2-(4-PROPYL-4-PIPERIDYLOXY)-ETHANOL 10.7 g of 2-(1-benzyl-4-propyl-4-piperidyloxy) ethanol [obtained by passing through a suspension of the hydrochloride of A in anhydrous ether a stream of ammonia] dissolved in 200 ml of absolute ethanol was reacted with hydrogen at 50° C in the presence of 1 g of 10% palladized charcoal until the theoretical amount of hydrogen was absorbed and then, the catalyst was filtered off. The ethanol was evaporated to obtain 6.1 g of 2-(4-propyl-4-piperidyloxy)-ethanol melting at 72° C.

For analysis, the product was crystallized from cyclohexane to obtain white crystals melting at 76° C and soluble in chloroform.

Analysis: $C_{10}H_{21}NO_2$; molecular weight = 187.28; Calculated: %C 64.13; %H, 11.30; %N 7.48; Found: %C, 63.8; %H, 11.6; %N, 7.3.

EXAMPLE X

PREPARATION OF 2-(4-HEPTYL-4-PIPERIDYLOXY)-ETHANOL

STEP A: 2-(1-BENZYL-4-HEPTYL-4-PIPERIDYLOXY)-ETHANOL

A solution of 101.5 g of n-heptyl bromide in 300 ml was added over 1 hour under a nitrogen atmosphere to a flask containing 9.6 g of magnesium turnings, 50 ml of ether, 3 drops of ethyl iodide and an iodine crystal and the mixture was stirred for 1 hour. A solution of 46.6. g of 8-benzyl-1,4-dioxa-8-azaspiro [4,5] decane in 1 liter of anhydrous benzene was added to the resulting solution and after removal of the ether, the mixture was refluxed for 16 hours. The solution was then cooled and 20 ml of water followed by 400 ml of a saturated aqueous ammonium chloride solution was added with stirring. The organic phase was decanted and the solvent was distilled under reduced pressure. The residue was rectified to obtain 40 g of 2-(1-benzyl-4-heptyl-4-piperidyloxy)-ethanol as an oil distilling between 150° to 200° C. The oil was used as is for the next step.

STEP B: 2-(4-HEPTYL-4-PIPERIDYLOXY)-ETHANOL

A solution of 40 g of 2-(1-benzyl-4-heptyl-4-piperidyloxy)-ethanol in 300 ml of absolute ethanol was reacted with hydrogen at 50° C in the presence of 0.4 g of 5% palladized charcoal until the theoretical amount of hydrogen was absorbed and the catalyst was then filtered off. The ethanol was distilled off and the residue was rectified to obtain 10.6 g of 2-(4-heptyl-4-piperidyloxy)-ethanol as a colorless oil boiling at 110°–130° C at 0.1 mm Hg.

Analysis: $C_{14}H_{29}NO_2$; molecular weight = 243.4; Calculated: %N, 5.53; Found: %N, 5.8.

EXAMPLE XI

First, 5 g (0.05 mole) of triethylamine and then 7.25 g (0.05 mole) of 2-(4-piperidyloxy)-ethanol were added to a solution of 13.75 g (0.05 mole) of 10-(3-chloropropyl)-phenothiazine in 200 ml of anhydrous toluene and the mixture was refluxed for 72 hours. After cooling, the triethylamine hydrochloride was removed by vacuum filtration and the toluene filtrate was washed with water and extracted with aqueous hydrochloric acid. The acidic solution was made alkaline and then was extracted with benzene. The benzene phase was washed several times with water, was dried and concentrated to obtain 8.4 g of an oil. The oil was dissolved in ether and hydrogen chloride in ether was added thereto. The precipitate was recoved by vacuum filtration and recrystallized from a mixture of 95% ethanol-ether to obtain 7.4 g (35% yield) of 10-[3-(4-β-hydroxyethoxypiperidino)-propyl]-phenothiazine hydrochloride in the form of white crystals melting at 183° C on a heated microscopic stage.

Analysis: $C_{22}H_{29}ClN_2O_3S$; Calculated: %C, 62.87; %H, 6.9; %N, 6.7; %Cl, 8.3; Found: %C, 62.7; %H, 6.9; %N, 6.5; %Cl, 8.3.

EXAMPLE XII

10-[3-(4-β-HYDROXYETHOXYPIPERIDINO)-PROPYL]-PHENOTHIAZINE HYDROCHLORIDE 22.5 g (0.15 mole) of sodium iodide was added to a solution of 41.5 g (0.15 mole) of 10-(3-chloropropyl)-phenothiazine in 400 ml of methyl ethyl ketone and then 15.2 g (0.15 mole) of triethylamine followed by 21.7 g (0.15 mole) of 2-(4-piperidyloxy)-ethanol were added to the reaction mixture. The solution was refluxed with stirring for 20 hours and after cooling, the precipitate formed was removed by vacuum filtration. The filtrate was evaporated to dryness and the oily residue was extracted with aqueous hydrochloric acid. The acidic extract was washed with ether, made alkaline and was extracted with benzene. The benzene phase was repeatedly washed with water, dried and concentrated to obtain an oil. The oil was dissolved in ether and hydrogen chloride in ether was added thereto. The precipitate was recoved by vacuum filtration and was crystallized from a 95% ethanol-ether mixture to obtain 35 g (55% yield) of 10-[3-(4-β-hydroxyethoxypiperidino)-propyl]-phenothiazine hydrochloride in the form of white crystals melting at 183° C on a heated microscopic stage. The product was identical to that of Example XI.

EXAMPLE XIII

10-[3-(4-[β-HYDROXYETHOXY]-PIPERIDINO)-PROPYL]-2-TRIFLUOROMETHYL-PHENOTHIAZINE HYDROCHLORIDE 17.6 g (0.117 mole) of sodium iodide were added to a solution of 40 g (0.17 mole) of 10-(3-chloropropyl)-2-trifluoromethyl-phenothiazine in 350 ml of methyl ethyl ketone followed by the addition of first 11.8 g (0.117 mole) of triethylamine and then 17 g (0.117 mole) of 2-(4-piperidyloxy)-ethanol. The resulting solution was refluxed for 20 hours and after cooling, the precipitate was removed by vacuum filtration. The filtrate was evaporated to dryness. The oil residue was stirred with a mixture of ether and dilute hydrochloric acid and the precipitate formed was recovered by vacuum filtration and crystallized from a 95% ethanol-ether mixture to obtain 40.5 g (71% yield) of 10-[3-(4-β-hydroxyethoxypiperidino) propyl]-2-trifluoromethyl-phenothiazine hydrochloride in the form of white crystals melting at 218°–219° C on a heated microscopic stage.

Analysis: $C_{23}H_{28}ClF_3N_2O_2S$; Calculated: %C, 56.5; %H, 5.7; %N, 5.7; %S, 6.6; Found: %C, 56.5; %H, 5.9; %N, 5.7; %S, 6.5.

EXAMPLE XIV

10-[3-(4-β-HYDROXYETHOXYPIPERIDINO)-PROPYL]-2-TRIFLUOROMETHYLPHENOTHIAZINE ACID SUCCINATE

A rapid stream of ammonia was passed for 1 hour through a suspension of 20 g of 10-[3-(4-[β-hydroxyethoxy]-piperidino) -propyl]-2-trifluoromethyl-phenothiazine hydrochloride in 200 ml of anhydrous ether and the solid formed was removed by vacuum filtration. The filtrate was evaporated to dryness and the oil residue was dissolved in absolute ethanol. 5 g of succinic acid were added to the solution and the mixture was allowed to stand for 48 hours. The precipitate formed was recovered by vacuum filtration and was crystallized from an absolute ethanol-ether mixture to obtain 12 g (52% yield) of the acid succinate of 10-[3-(4-β-hydroxyethoxy-piperidino)-propyl]-2-trifluoromethyl-phenothiazine in the form of white crystals melting at 112° C on a heated microscopic stage.

Analysis: $C_{27}H_{33}F_3N_2O_6S$; Calculated: %C, 56.8; %H, 5.8; %N, 4.9; %S, 5.6; Found: %C, 56.9; %H, 5.7; %N, 4.8; %S, 5.7.

EXAMPLE XV

2-CHLORO-10-[3-(4-β-HYDROXYETHOXYPIPERIDINO)-PROPYL]-PHENOTHIAZINE HYDROCHLORIDE

Using the procedure of Example XII, 36.3 g (0.117 mole) of 2-chloro-10-(3-chloropropyl)-phenothiazine were reacted and crystallization from an absolute ethanol-ether mixture gave 30 g (55% yield) of 2-chloro-10-[3-(4-βhydroxyethoxy-piperidino)-propyl]-phenothiazine hydrochloride in the form of white crystals melting at 200°–202° C on a heated microscopic stage.

Analysis: $C_{22}H_{28}Cl_2N_2O_2S$; Calculated: %C, 58.0; %H, 6.2; %N, 6.2; %S, 7.0; %Cl, 15.6; Found: %C, 58.0, %H, 6.3; %N, 6.0; %S, 7.1; %Cl, 15.4.

EXAMPLE XVI

2-TRIFLUOROMETHYL-10-[3-(4-[1,2-DIMETHYL-2-HYDROXYETHOXY]-PIPERIDINO)-PROPYL]-PHENOTHIAZINE 22.5 g (0.15 mole) of sodium iodide were added to a solution of 51.5 g (0.15 mole) of 10-(3-chloropropyl)-2-trifluoromethyl-phenothiazine in 400 ml of methyl ethyl ketone followed by the addition of 15.2 g (0.15 mole) of triethylamine and then 26 g (0.15 mole) of 1,2-dimethyl-2-(4-piperidyloxy)-ethanol. The mixture was then refluxed for 20 hours and after cooling, the precipitate formed was removed by vacuum filtration. The filtrate was evaporated to dryness and the oil residue was chromatographed over 1 kg of neutral alumina. Elution with ethyl acetate gave 34.5 g (48% yield) of 2-trifluoromethyl-10-[3-(4-[1,2-dimethyl-2-hydroxyethoxy]-piperidino)-propyl]-phenothiazine in the form of a clear amber oil.

Analysis: $C_{25}H_{31}F_3N_2O_2S$; Calculated: %C, 62.5; %H, 6.5; %N, 5.8; %S, 6.7; Found: %C, 62.7; %H, 6.6; %N, 5.8; %S, 6.7.

EXAMPLE XVII

2-METHOXY-10-[3-(4-β-HYDROXYETHOXYPIPERIDINO)-PROPYL]-PHENOTHIAZINE HYDROCHLORIDE

Using the procedure of Example XII, 36.5 g (0.12 mole) of 2-methoxy-10-(3-chloropropyl)-phenothiazine were reacted and crystallization of the product from an absolute ethanol-ether mixture gave 34 g (63% yield) of 2-methoxy-10-[4-β-hydroxyethoxypiperidino)-propyl]-phenothiazine hydrochloride in the form of white crystals melting at 155° C on a heated microscopic stage.

Analysis: $C_{23}H_{31}ClN_2O_3S$; Calculated: %C, 61.2; %H, 6.9; %N, 6.2; %S, 7.1; %Cl, 7.9; Found: %C, 61.3; %H, 7.2; %N, 6.2; %S, 7.1; %Cl, 7.8.

EXAMPLE XVIII

2-TRIFLUOROMETHYL-10-[3-(4-β-HYDROXYPROPOXYPIPERIDINO)-PROPYL]-PHENOTHIAZINE ACID OXALATE

Using the procedure of Example XII, 24.8 g (0.072 mole) of 2-trifluoromethyl-10-(3-chloropropyl)-phenothiazine and 11.5 g (0.072 mole) of 3-(4-piperidyloxy)-propanol were reacted to form 30 g of 2-trifluoromethyl-10-[3-(4-β-hydroxypropoxypiperidino)-propyl]-phenothiazine in the form of an oil. The oil was dissolved in absolute ethanol and 8 g of oxalic acid were added to the resulting solution. The precipitate formed was recovered by vacuum filtration and was crystallized from acetone to obtain 18 g (60% yield) of the acid oxalate of the said phenothiazine in the form of white crystals melting at 124°–126° C on a heated microscopic stage.

Analysis: $C_{26}H_{31}F_3N_2O_6S$ Calculated: %C, 56.1; %H 5.6; %N 5.0; %S, 5.8; Found: %C, 56.2; %H, 5.5; %N, 5.0 %S, 5.8.

EXAMPLE XIX

Using the procedure of Example XII, 19.5 g (0.0675 mole) of 10-(3-chloro-2-methyl-propyl)-phenothiazine were reacted and crystallization from acetone gave 9.5 g (32% yield) of 10-[2-methyl-3-[4-β-hydroxyethoxypiperidino]-propyl]-phenothiazine hydrochloride in the form of white crystals melting at 105°–108° C on a heated microscopic stage.

Analysis: $C_{23}H_{31}ClN_2O_2S$; Calculated: %C, 63.3; %H, 7.2; %N, 6.4; %S, 7.4; %Cl, 8.2; Found: %C, 62.9; %H, 7.4; %N, 6.2; %S, 7.3; %Cl, 8.2.

EXAMPLE XX

2-CHLORO-10-[2-METHYL-3-(4-β-HYDROXYETHOXYPIPERIDINO)-PROPYL]-PHENOTHIAZINE HYDROCHLORIDE

Using the process of Example XII, 30 g (0.0925 mole) of 2-chloro-10-(2-methyl-3-chloro-propyl)-phenothiazine were reacted and crystallization of the product from absolute ethanol gave 12.2 g (28% yield) of 2-chloro-10-[2-methyl-3-(4-β-hydroxyethoxypiperidino)-propyl]-phenothiazine hydrochloride in the form of white crystals melting at 212° C.

Analysis: $C_{23}H_{30}Cl_2N_2O_2S$; Calculated: %C, 58.8; %H, 6.4; %N, 6.0; %S, 6.8; %Cl, 15.1; Found: %C, 58.9; %H, 6.7; %N, 5.6; %S, 6.8; %Cl, 14.9.

EXAMPLE XXI

Using the procedure of Example XI, 4.7 g (0.0147 mole) of 10-(2-bromopropyl)-phenothiazine were reacted and crystallization of the product from acetonitrile gave 3.6 g (58% yield) of 10-[2-(4-β-hydroxyethoxypiperidino)-propyl]-phenothiazine hydrochloride in the form of white crystals melting at 204°–209° C.

Analysis: $C_{22}H_{29}ClN_2O_2S$; Calculated: %C, 62.8; %H, 6.9; %N, 6.7; %S, 7.6; %Cl, 8.4; Found: %C, 62.3; %H, 7.1; %N, 6.8; %S, 7.5; %Cl, 8.6.

EXAMPLE XXII

Using the procedure of Example XII, 22.4 g (0.0855 mole) of 10-(2-chloroethyl)-phenothiazine were reacted and crystallization of the product from acetonitrile gave 10.6 g (30% yield) of 10-[2-(4-β-hydroxyethoxypiperidino)-ethyl]-phenothiazine hydrochloride in the form of white crystals melting at 175°–178° C.

Analysis: $C_{21}H_{27}ClN_2O_2S$; Calculated: %C, 62.0; %H, 6.7; %N, 6.9; %S, 7.9; %Cl, 8.7; Found: %C, 62.2; %H, 6.7; %N, 6.8; %S, 8.0; %Cl, 8.3.

EXAMPLE XXIII

2-METHYLTHIO-10-[3-(4-β-HYDROXYETHOXYPIPERIDINO)-PROPYL]-PHENOTHIAZINE HYDROCHLORIDE 1-bromo-3-chloro-propane and 2-methylthio-phenothiazine were reacted in heptane in the presence of sodium amide and the product was purified by chromatography to obtain 2-(methylthio-10-(3-chloropropyl)-phenothiazine melting at 58° C.

Analysis: $C_{16}H_{16}ClNS_2$; Calculated: %C, 59.7; %H, 5.0; %Cl, 11.0; Found: %C, 59.8; %H, 4.9; %Cl, 11.0.

7 g (0.0469 mole) of sodium iodide were added to a solution of 15.1 g (0.0469 mole) of 2-methylthio-10-(3-chloropropyl)-phenothiazine in 250 ml of methyl ethyl ketone followed by the addition of 4.74 g (0.0469 mole) of triethylamine and then 6.8 g (0.0469 mole) of 2-(4-piperidyloxy)-ethanol. The mixture was refluxed for 20 hours and after cooling, the precipitate formed was removed by filtration. The filtrate was evaporated to dryness and the oil residue was dissolved in methylene chloride. The organic phase was washed with aqueous sodium bicarbonate, then with water, dried and concentrated. The resulting oil was dissolved in ethanol and an ether solution of hydrogen chloride was added thereto. The precipitate formed was recovered by vacuum filtration and twice crystallized from an ether-absolute ethanol mixture to obtain 9 g (41% yield) of 2-methylthio-10-[3-(4-β-hydroxyethoxypiperidino)propyl]-phenothiazine hydrochloride in the form of white crystals melting at 158°–160° C.

Analysis: $C_{23}H_{31}ClN_2O_2S_2$ Calculated: %C, 59.1; %H, 6.7; %N, 6.0; %S, 13.7; %Cl, 7.6; Found: %C, 58.8; %H, 6.8; %N, 6.0; %S, 13.7; %Cl, 7.3.

EXAMPLE XXIV

Using the process of Example XI, 9.5 g (0.0297 mole) of 2-methoxy-10-(2-methyl-3-chloropropyl)-phenothiazine were reacted to form 2-methoxy-10-[2-methyl-3-(4-β-hydroxyethoxypiperidino)-propyl]-phenothiazine as an oil which was dissolved in ether. Ethereal hydrochloric acid was added to the solution and precipitate formed was recovered by vacuum filtration. The product was crystallized from an ether-absolute ethanol mixture to obtained 4.8 g (35% yield) of the corresponding hydrochloride in the form of white crystals melting at 207° C. Analysis: $C_{24}H_{33}ClN_2O_3S$; Calculated: %C, 62.0; %H, 7.2; %N, 6.0; %Cl, 7.6; %S, 6.9; Found: %C, 62.0; %H, 7.3; %H, 6.0; %Cl, 7.4; %S, 7.0.

EXAMPLE XXV

Using the procedure of Example XI, 49.7 g (0.145 mole) of 2-trifluoromethyl-10-(3-chloropropyl)-phenothiazine and 25.5 g (0.145 mole) of 4-(4-piperidyloxy)-butanol were reacted to obtain 29 g (39% yield) of 2-trifluoromethyl-10-[3-(4-[4-hydroxybutoxy]-piperidino)-propyl]-phenothiazine hydrochloride in the form of white crystals melting at 67° C.

Analysis: $C_{25}H_{32}ClF_3N_2O_2S$; Calculated: %C, 58.1; %H, 6.2; %N, 5.4; %S, 6.2; %Cl 6.9; Found: %C, 58.0; %H, 6.4; %N, 5.5; %S, 6.3; %Cl, 6.7.

EXAMPLE XXVI

A solution of 5.36 g (0.04 mole) of hexanoyl chloride in 50 ml of anhydrous benzene was added dropwise to a solution of 18.1 g (0.04 mole) of 2-trifluoromethyl-10-[3-(4-β-hydroxyethoxypiperidino)-propyl]-phenothiazine (prepared as in Example XIII) in 150 ml of anhydrous benzene containing 4.04 g (0.04 mole) of triethylamine. The mixture was stirred for 48 hours at room temperature and the solid was filtered off. The benzene filtrate was washed with aqueous N sodium bicarbonate, then with water, dried and concentrated. The oil residue was dissolved in ether and ethereal hydrogen chloride was added thereto. The precipitate of unreacted starting material in its hydrochloride form was removed by vacuum filtration and ammonia was bubbled through the ether filtrate and the ammonium chloride formed was removed by filtration. The filtrate was evaporated to dryness to obtain 15 g (68% yield) of 2-trifluoromethyl-10-[3-(4-β-hexanoyloxyethoxypiperidino)-propyl]-phenothiazine as a clear amber oil.

Analysis: $C_{29}H_{37}F_3N_2O_3S$; Calculated: %C, 63.2; %H, 6.8; %N, 5.1; %S, 5.8; Found: %C, 63.3; %H, 7.0; %N, 4.9; %S, 5.8.

EXAMPLE XXVII

Using the procedure of Example XXVI, 5.26 g (0.0353 mole) of heptanoyl chloride were reacted to obtain 8.2 g (41% yield) of 2-trifluoromethyl-10-[3-(4-β-heptanoyloxyethoxypiperidino)-propyl]-phenothiazine as a clear amber oil.

Analysis: $C_{30}H_{39}F_3N_2O_3S$ Calculated: %C, 63.8; %H, 7.0; %N, 5.0; %S, 5.7; Found: %C, 63.8; %H, 7.2; %N, 4.9; %S, 5.8.

The latter product was dissolved in absolute ethanol and then a stoichiometric amount of oxalic acid was added thereto and the product was crystallized from 95% ethanol to obtain 2-trifluoromethyl-10-[3-(4-β-heptanoyloxyloxyethoxypiperidino) -propyl]-phenothiazine acid oxalate melting at 150° C.

Analysis: $C_{32}H_{41}F_3N_2O_7S$; Calculated: %C, 58.7; %H, 6.3; %N, 4.3; %S, 4.9; Found: %C, 58.8; %H, 6.4; %N, 4.3; %S, 4.9.

EXAMPLE XXVIII

Using the procedure of Example XXVI, 6.48 g (0.04 mole) of octanoyl chloride were reacted to give 10.2 g (44% yield) of 2-trifluoromethyl-10-[3-(4-β-octanoyloxyethoxypiperidino)-propyl]-phenothiazine as a clear amber oil.

Analysis: $C_{31}H_{41}F_3N_2O_3S$; Calculated: %C, 64.3; %H, 7.1; %N, 4.8; %S, 5.5; Found: %C, 64.5; %H, 7.4; %N, 4.8; %S, 5.4.

EXAMPLE XXIX

Using the procedure of Example XXVI, 7.05 g (0.04 mole) of nonanoyl chloride were reacted to obtain 12 g (50% yield) of 2-trifluoromethyl-10-[3-(4-β-nonanoyloxyethoxypiperidino)-propyl]-phenothiazine as a clear amber oil.

Analysis: $C_{32}H_{43}F_3N_2O_3S$; Calculated: %C, 64.8; %H, 7.3; %N, 4.7; %S, 5.4; Found: %C, 64.8; %H, 7.4; %N, 4.7; %S, 5.5.

EXAMPLE XXX

Using the procedure of Example XXVI, 3.45 g (0.0182 mole) of decanoyl chloride were reacted to obtain 7.8 (70% yield) of 2-trifluoromethyl-10-[3-(4-β-decanoyloxyethoxypiperidino)-propyl]-phenothiazine as a clear amber oil.

Analysis: $C_{33}H_{45}F_3N_2O_3S$; Calculated: %C, 65.3; %H, 7.5; %N, 4.6; %S, 5.3; Found: %C, 65.5; %H, 7.5; %N, 4.6; %S, 5.3.

EXAMPLE XXXI 25.3 g (1.1 mole) of sodium dissolved in 464.8 g (4 mole) of heptyl alcohol was heated to 150° C and 54 g (0.49 mole) of 3-chloropropionic acid were added thereto dropwise with stirring. The mixture was heated for a further 2 hours and a precipitate appeared. The mixture was cooled and 1.5 liters of water were added. The mixture was extracted with ether and the aqueous phase was acidified with concentrated sulfuric acid. The mixture was extracted with ether and the ether phase was washed with water, dried and was concentrated. The residue was rectified to obtain 49 g (52% yield) of 3-heptyloxy-propionic acid as a colorless oil boiling at 165° C at 15 mm Hg and having a refractive index $n_D^{22} = 1.436$.

Analysis: $C_{10}H_{20}O_3$; Calculated: %C, 63.8; %H, 10.7; Found: %C, 64.2; %H, 10.9.

49 g of the said acid dissolved in 75 ml of thionyl chloride was refluxed for 3 hours and the thionyl chloride was evaporated off. The residue was rectified to obtain 40.5 g (76% yeild) of 3-heptyloxy-propionyl chloride as a clear yellow liquid boiling at 76° C at 0.01 mm Hg and having a refractive index $n_D^{22} = 1.437$.

Analysis: $C_{10}H_{19}ClO_2$; Calculated: %Cl, 17.2; Found: %Cl, 17.6.

Using the procedure of Example XXVI, 8.26 g (0.04 mole) of 3-heptyloxy-propionic acid chloride were reacted to form 14.9 g (60% yield) of 2-trifluoromethyl-10-[3-(4-δ-heptyloxypropionyloxyethoxypiperidino)-propyl]-phenothiazine as a clear amber oil.

Analysis: $C_{33}H_{45}F_3N_2O_4S$; Calculated: %C, 63.6; %H, 7.3; %N, 4.5; %S, 5.2; Found: %C, 63.7; %H, 7.5; %N, 4.4; %S, 5.1.

EXAMPLE XXXII

Using the procedure of Example XXVI, 8.08 g (0.04 mole) of 9-undecylenoyl chloride were reacted to obtain 7.3 g (30% yield) of 2-trifluoromethyl-10-[3-(4-[9-undecylenoyloxyethoxy-]piperidino)-propyl]-phenothiazine as a clear amber oil.

Analysis: $C_{34}H_{15}F_3N_2O_3S$; Calculated: %C, 66.0; %H, 7.3; %N, 4.5; %S, 5.2; Found: %C, 66.2; %H, 7.4; %N, 4.5; %S, 5.2.

Using the procedure of Example XXVII, the latter base was reacted with oxalic acid to obtain the corresponding acid oxalate which after crystallization from an ether-acetone mixture melted at 122° C.

Analysis: $C_{36}H_{47}F_3N_2O_7S$; Calculated: %C, 61.0; %H, 6.7; %N, 4.0; %S, 4.5; Found: %C, 61.1; %H, 6.9; %N, 3.9; %S, 4.6.

EXAMPLE XXXIII

Using the procedure of Example XXVI, 12.9 g (0.0269 mole) of 2-trifluoromethyl-10-[3-(4-[4-hydroxybutoxy-piperidino)-propyl]-phenothiazine (prepared in Example XV) and 5.65 g (0.0298 mole) of decanoyl chloride were reacted to obtain 8 g (47% yield) of 2-trifluoromethyl-10-[3-(4-[4-decanoyloxybutoxy]-piperidino)-propyl]-phenothiazine as a clear amber oil.

Analysis: $C_{35}H_{49}F_3N_2O_3S$; Calculated: %C, 66.2; %H, 7.8; %N, 4.4; %S, 5.1; Found: %C, 66.1; %H, 7.9; %N, 4.4; %S, 5.1.

The latter base was reacted as in Example XXVII to obtain the acid oxalate thereof which after crystallization from an ether-ethanol mixture melted at 120° C.

Analysis: $C_{37}H_{51}F_3N_2O_7S$; Calculated: %C, 61.3; %H, 7.1; %N, 3.9; Found: %C, 61.4; %H, 7.0; %N, 4.0.

EXAMPLE XXXIV

Using the procedure of Example XXVI, 15.2 g (0.0553 mole) of hexadecanoyl chloride were reacted to obtain 11.5 g (30% yield) of 2-trifluoromethyl-10-{3-[4-(2-hexadecanoyloxyethoxy)-piperidino]-propyl}-phenothiazine as a clear amber oil.

Analysis: $C_{39}H_{57}F_3N_2O_3S$; Calculated: %C, 67.8; %H, 8.3; %N, 4.1; %S, 4.6; Found: %C, 67.7; %H, 8.5; %N, 3.9; %S, 4.5.

The said base was reacted as in Example XXVII to obtain the acid oxalate thereof which after crystallization from 95% ethanol melted at 130° C.

Analysis: $C_{41}H_{59}F_3N_2O_7S$; Calculated: %C, 63.1; %H, 7.6; %N, 3.6; %S, 4.1; Found: %C, 63.0; %H, 7.8; %N, 3.5; %S, 4.2.

EXAMPLE XXXV 31 g (0.081 mole) of 10-[3-(4-β-hydroxyethoxypiperidino)-propyl]-phenothiazine (prepared as in Example XII) were dissolved in 200 ml of anhydrous benzene containing 8.2 g (0.081 mole) of triethylamine and a solution of 15.4 g (0.081 mole) of decanoyl chloride in 100 ml of anhydrous benzene was added dropwise thereto. The mixture was agitated for 48 hours at room temperature and the formed precipitate was removed by vacuum filtration. The benzene filtrate was washed with an aqueous sodium bicarbonate solution and then with water. After drying and concentration of the benzene solution, the oil residue was dissolved in ether and an ethereal hydrogen chloride solution was added. The precipitate was recovered by vacuum filtration and twice crystallized from absolute ethanol to obtain 10-[3-(4-β-decanoyloxyethoxypiperidino)-propyl]-phenothiazine hydrochloride as white hygroscopic crystals.

The precipitate was suspended in anhydrous ether and a stream of ammonia was bubbled into it. The formed ammonium chloride was removed by filtration and the ether was evaporated to obtain 20 g (46% yield) of 10-[3-(4-β-decanoyloxyethoxypiperidino)-propyl]-phenothiazine as a clear amber oil.

Analysis: $C_{32}H_{46}N_2O_3S$; Calculated: %C, 71.3; %H, 8.6; %N, 5.2; %S, 6.0; Found: %C, 71.5; %H, 8.8; %N, 5.2; %S, 5.8.

The said hydrochloride prepared as indicated above was isolated and crystallized from absolute ethanol. It had an instantaneous melting point of 50° C (hygroscopic).

Analysis: $C_{32}H_{47}ClN_2O_3S$; Calculated: %C, 66.8; %H, 8.2; %N, 4.9; %S, 5.6; %Cl, 6.2; Found: %C, 6.9; %H, 8.3; %N, 4.8; %S, 5.7; %Cl, 6.3.

EXAMPLE XXXVI

Using the procedure of Example XXXV, 18.7 g (0.04 mole) of 2-trifluoromethyl-10-[3-(4-β-hydroxyethoxy-piperidino)-propyl]-phenothiazine (prepared in Example XXIII) and 9.2 g (0.04 mole) of 3,4,5-trimethoxybenzoyl chloride were reacted to obtain 8.5 g (33% yield) of 2-trifluoromethyl-10-[3{4-[2-(3,4,5-trimethoxy-benzoyloxy)-ethoxy]-piperidino}-propyl]-phenothiazine as a clear amber oil Analysis: $C_{33}H_{37}F_3N_2O_6S$; Calculated: %C, 61.3; %H, 5.8; %N, 4.3; %S, 5.0; Found: %C, 61.5; %H, 5.9; %N, 4.2; %S, 5.0.

EXAMPLE XXXVII

Using the procedure of Example XXXV, 18.7 g (0.04 mole) of 2-trifluoromethyl-10-[3-(4-{3-hydroxypropoxy}-piperidino)-propyl]-phenothiazine (prepared in Example XVIII) and 3.14 g (0.04 mole) of acetyl chloride were reacted to obtain 10 g (49% yield) of 2-trifluoromethyl-10-[3-(4-{3-acetoxypropoxy}-piperidino)-propyl]-phenothiazine as a clear amber oil.

Analysis: $C_{26}H_{31}F_3N_2O_3S$; Calculated: %C, 61.4; %H, 6.1; %N, 5.5; %S, 6.3; Found: %C, 61.3; %H, 6.2; %N, 5.6; %S, 6.4.

EXAMPLE XXXVIII

Using the procedure of Example XXXV, 14.8 g (0.0308 mole) of 2-trifluoromethyl-10-[3-(4-{4- hydroxybutoxy}-piperidino-propyl]-phenothiazine (prepared in Example XXV) and 2.65 g (0.0338 mole) of acetyl chloride were reacted to obtain 10.6 g (66% yield) of 2-trifluoromethyl-10-[3-(4-{4-acetoxybutoxy}-piperidino)-propyl]-phenothiazine as a clear amber oil.

Analysis: $C_{27}H_{33}F_3N_2O_3S$; Calculated: %C, 62.0; %H, 6.4; %N, 5.4; %S, 6.1; Found: %C, 62.0; %H, 6.5; %N, 5.2; %S, 6.1.

EXAMPLE XXXIX 6.16 g (0.0412 mole) of sodium iodide, 14.1 g (0.0412 mole) of 2-trifluoromethyl-10-(3-chloropropyl)-phenothiazine, 11.2 g (0.0412 mole) of 2-(4-piperidyloxy)-ethyl octanoate and 4.16 g (0.0412 mole) of triethylamine were successively dissolved in 250 ml of methyl ethyl ketone. The mixture was refluxed for 20 hours with agitation and after cooling, the formed precipitate was removed by filtration. The filtrate was evaporated to dryness and the oil residue was dissolved in methylene chloride. This organic solution was washed with an aqueous solution of sodium bicarbonate, then with water, dried and concentrated. The oil residue was dissolved in ether and an ether solution of hydrogen chloride was added thereto which caused the precipitation of unreacted 2-(4-piperidyloxy)-ethyl octanoate as its hydrochloride. This precipitate was vacuum filtered and ammonia gas bubbled through the ether filtrate. The ammonium chloride formed was removed by vacuum filtration and the ether was evaporated from the filtrate to obtain 17.8 g (75% yield) of 2-trifluoromethyl-10-[3-(4-{2-octanoyloxyethoxy}-piperidino)-propyl]-phenothiazine as a clear amber oil.

The infrared spectrum and the thin-layer chromatography indicate that this product is identical to that obtained in Example XXVIII.

EXAMPLE XL

Using the procedure of Example XXXIX, 17.5 g (0.093 mole) of 2-(4-piperidyloxy)-ethyl acetate were reacted to obtain 9.7 g (21% yield) of 2-trifluoromethyl-10-[3-(4-{2-acetoxyethoxy}-piperidino-propyl]-phenothiazine as a clear amber oil.

Analysis: $C_{25}H_{29}F_3N_2O_3S$; Calculated: %C, 60.7; %H, 5.9; %N, 5.7; %S, 6.5; Found: %C, 60.9; %H, 6.0; %N, 5.6; %S, 6.5.

EXAMPLE XLI

Using the procedure of EXAMPLE XXVI, 7.27 g (0.0407 mole) of heptyl chloroformate were reacted to 8.9 g (37% yield) of 2-trifluoromethyl-10-[3-(4--heptyloxycarbonyloxyethoxypiperidino)-propyl]-phenothiazine as a clear amber oil.

Analysis: $C_{31}H_{41}F_3N_2O_4S$; Calculated: %C, 62.6; %H, 7.0; %N, 4.7; %S, 5.4; Found: %C, 62.8; %H, 7.1; %N, 4.7; %S, 5.4.

As in Example XXVII, the said base was reacted with oxalic acid to form the acid oxalate thereof which melted at 114° C after crystallization from an acetone-ether mixture.

Analysis: $C_{33}H_{43}F_3N_2O_8S$; Calculated: %C, 57.8; %H, 6.3; %N, 4.1; %S, 4.7; Found: %C, 58.0; %H, 6.3; %N, 4.1; %S, 4.7.

EXAMPLE XLII

Undecyl chloroformate was prepared by the method described by NAJER et al. [Bull. Soc. Chim., 1955, p. 1189] by reaction of a toluene solution of phosgene with undecylic alcohol. The product boiled at 95°-100° C at 0.05 mm Hg and had a refractives index $n_D^{23} = 1.437$.

Analysis: $C_{12}H_{23}ClO_2$; Calculated: %Cl, 15.1; Found: %Cl, 15.5.

Using the procedure of Example XXVI, 9.6 g (0.0407 mole) of undecyl chloroformate were reacted to obtain 8 g (30% yield) of 2-trifluoromethyl-10-[3-(4-β-undecyloxycarbonyloxyethoxypiperidino)-propyl]-phenothiazine as a clear amber oil.

Analysis: $C_{35}H_{49}F_3N_2O_4S$; Calculated: %C, 64.6; %H, 7.6; %N, 4.3; %S, 4.9; Found: %C, 64.3; %H, 7.6; %N, 4.4; %S, 4.9.

As in Example XXVII the said base, prepared above, was reacted with oxalic acid to obtain the corresponding acid oxalate which melted at 115° C after crystallization from 95% ethanol.

Analysis: $C_{37}H_{51}F_3N_2O_8S$; Calculated: %C, 60.0; %H, 6.9; %N, 3.8; %S, 4.3; Found: %C, 59.3; %N, 6.9; %N, 3.8; ; %S, 4.4.

EXAMPLE XLIII

STEP A: 2-TRIFLUOROMETHYL-10[3-(4-β-HYDROXYETHOXYPIPERIDINO)-PROPYL]-PHENOTHIAZINE 40 g of 2-trifluoromethyl-10-(3-chloropropyl)-phenothiazine were dissolved in 350 ml of methyl ethyl ketone and 17.6 g of sodium iodide, 11.8 g of triethylamine, then 17 g of 2-(4-piperidyloxy)-ethanol were successively added to this solution. It was refluxed for 20 hours and after cooling, the precipitate was removed by vacuum filtration. The filtrate was evaporated to dryness to obtain 2-trifluoromethyl-10-[3-(4-β-hydroxyethoxypiperidino)-propyl]-phenothiazine as an oil which was added to a mixture of ether and dilute hydrochloric acid. The formed precipitate was recovered by vacuum filtration and was crystallized from 95% ethanol to obtain 40.5 g of 2-trifluoromethyl-10-[-3(4-β-hydroxyethoxypiperidino)-propyl]-phenothiazine hydrochloride as white crystals. Then a current of ammonia was led into an ether suspension of this product and the formed precipitate was removed by filtration. The filtrate was evaporated to dryness to obtain 2-trifluoromethyl-10-[3-(4-β-hydroxyethoxypiperidino)-propyl]-phenothiazine as an oil.

STEP B: 2-TRIFLUOROMETHYL-10-[3-(4-β-PROPIONYLOXYETHOXYPIPERIDINO)-PROPYL]-PHENOTHIAZINE 22.6 g of 2-trifluoromethyl-10-[3-(4-β-hydroxyethoxypiperidino)-propyl]-phenothiazine were dissolved in a mixture of 185 ml of anhydrous benzene and 7 ml of triethylamine. A solution of 4.62 g of propionyl chloride in 60 ml of anhydrous benzene was added thereto and the mixture was stirred for 48 hours at room temperature. The formed precipitate was removed by filtration and the benzene filtrate was washed with an aqueous solution of sodium bicarbonate, then with water. After drying and concentration of the benzene solution, the obtained oil (25.3 g) was dissolved in ether and an ether solution of hydrogen chloride was added thereto. The unreacted starting material precipitated as its hydrochloride and this precipitate was removed by vacuum filtration. An ammonia current was bubbled into the ether filtrate and after removal of the formed ammonium chloride by filtration, the filtrate was evaporated to obtain 18 g of 2-trifluoromethyl-10-[3-(4-β-propionyloxyethoxypiperidino)-propyl]- phenothiazine as a clear amber oil soluble in ether and ethanol.

Analysis: $C_{26}H_{31}F_3N_2O_3S$; molecular weight = 508.6; Calculated: %C, 61.39; %H, 6.14; %N, 5.51; %S, 6.30; Found: %C, 61.36; %H, 6.30; %N, 5.60; %S, 6.30.

I.R. Spectrum: Presence of C=O ester at 1735cm$^{-1}$, of C=O at 1250 and 1080 cm$^{-1}$ and of —CF$_3$ at 1330, 1168 and 1120 cm$^{-1}$.

EXAMPLE XLIV 22.6 g of 2-trifluoromethyl-10-[3-(4-β-hydroxyethoxypiperidino)-propyl]-phenothiazine (prepared by Example XLIII) were dissolved in a mixture of 185 ml of anhydrous benzene and 7 ml of triethylamine. A solution of 5.32 g of butyryl chloride in 60 ml of benzene was added to this solution and the mixture was agitated for 48 hours at room temperature. The precipitate formed was removed and the benzene filtrate was washed with an aqueous solution of sodium bicarbonate, then with water. After drying and concentration of the benzene solution, the obtained oil was dissolved in ether and an ether solution of hydrogen chloride was added thereto. The unreacted starting material precipitated as its hydrochloride and was removed by vacuum filtration. Addition of a hydrogen chloride-ether solution precipitated the desired product as its hydrochloride. The product was suspended in ether and an ammonia stream was bubbled into the suspension. After removal of the formed ammonium chloride by filtration, evaporation of ether from the filtrate gave 5.7 g of 2-trifluoromethyl-10-[3-(4-β-butyryloxyethoxypiperidino)-propyl]-phenothiazine as a clear amber oil soluble in ether and ethanol.

Analysis: $C_{27}H_{33}F_3N_2OS$; molecular weight = 522.6; Calculated: %C, 62.05; ; %H, 6.36; %N, 5.36; %S, 6.13; Found: %C, 62.1; %H, 6.4; %N, 5.26; %S, 6.1.

I.R. Spectrum: Presence of C=O ester at 1733 cm$^{-1}$ and of —CF$_3$ at 1330, 1167 and 1120 cm$^{-1}$.

EXAMPLE XLV 22.6 g of 2-trifluoromethyl-10-[3-(4-β-hydroxyethoxypiperidino)-propyl]-phenothiazine (prepared by Example XLIII) were dissolved in a mixture of 180 ml of anhydrous benzene and 7 ml of triethylamine. A solution of 6.02 g of valeryl chloride in 60 ml of anhydrous benzene was added thereto and the mixture was agitated at room temperature for 48 hours. Then, the precipitate formed was removed by filtration and the filtrate was washed with an aqueous solution of sodium bicarbonate. After drying and concentrating the benzene solution, the obtained oil was dissolved in ether and an hydrogen chloride ether solution was added thereto. The unreacted starting material precipitated as its hydrochloride. The precipitate was removed by vacuum filtration, and addition of a hydrogen-chloride ether solution to the filtrate. The desired product was precipitated as its hydrochloride which was suspended in ether and a current of ammonia was bubbled into the suspension. After filtration to remove the formed ammonium chloride, the ether was evaporated to obtain 2-trifluoromethyl-10-[3(4-β-valeryloxyethoxypiperidino)-propyl]-phenothiazine. The latter was purified by forming the acid oxalate by addition of oxalic acid to an alcoholic solution of the base. The said oxalate was crystallized from 95% ethanol and then was suspended in ether and ammonia bubbled through. After filtration and evaporation of the ether, 8.9 g of the said product were obtained as a clear amber oil soluble in ether and ethanol.

Analysis: $C_{28}H_{35}F_3N_2OS$; molecular weight = 536.6; Calculated: %C, 63.67; %H, 6.58; %N, 5.22; %S, 5.97; Found: %C, 62.8; %H, 6.7; %N, 5.2; %S, 5.8.

I.R. Spectrum: Presence of C=O ester at 1735 cm$^{-1}$ and of —CF$_3$ at 1330, 1167 and 1121 cm$^{-1}$.

EXAMPLE XLVI 13.55 g of 2-trifluoromethyl-10-[3-(4-β-hydroxyethoxypiperidino)-propyl]-phenothiazine (prepared by Example XLIII), 5.4 ml of triethylamine and 100 ml of anhydrous benzene were added to a flask and a solution of 5.7 g of 2-methyl-heptanoic acid chloride in 50 ml of anhydrous benzene was added thereto. The mixture was agitated at room temperature for 24 hours and then the precipitate formed was removed by filtration. The benzene filtrate was washed with an aqueous solution of sodium bicarbonate, then with water. After drying and concentration of the benzene solution, the resulting oil was purified by chromatography on silica gel. After elution with ethanol and evaporation of the solvent, 5.2 g of 2-trifluoromethyl-10-[3-(4-β-{2-methylheptanoyloxy}ethoxypiperidino)-propyl]-phenothiazine as a clear oil were obtained.

Analysis: $C_{31}H_{41}F_3N_2O_3S$; molecular weight = 578.73; Calculated: %C, 64.33; %H, 7.14; %N, 4.84; %F, 9.85; %S, 5.54; Found: %C, 64.0; %H, 7.1; %N, 4.7; %F, 9.6; %S, 5.5.

I.R. Spectrum: Presence of C=O ester at 1733 cm$^{-1}$.

EXAMPLE XLVII 18.7 g of 2-trifluoromethyl-10-(3-chloropropyl)-phenothiazine were dissolved in 50 ml of methyl ethyl ketone and 8.12 g of sodium iodide, 5.5 g of triethylamine, and 8.7 g of 2-(4-methyl-4-piperidyloxy)-ethanol dissolved in 50 ml of methyl ethyl ketone was succesively added thereto. The mixture was refluxed for 20 hours and after cooling, the precipitate formed was removed by vacuum filtration. The filtrate was evaporated under reduced pressure and the residue was dissolved in methylene chloride. The organic solution was washed with an aqueous solution of sodium bicarbonate, then with water, dried and concentrated to dryness.

The 2-trifluoromethyl-10-[3-(4-β-hydroxyethoxy-4-methyl piperidino)-propyl]-phenothiazine was reacted in acetone with an ether solution of hydrogen chloride and the precipitate formed was recovered by vacuum filtration. The product was crystallized from acetone-ethanol mixture to obtain 9.1 g of 2-trifluoromethyl-10-[3-(4-β-hydroxyethoxy-4-methylpiperidino)-propyl]-phenothiazine hydrochloride as white crystals melting at 218° C and soluble in ethanol, slightly soluble in acetone and insoluble in ether and water.

Analysis: $C_{24}H_{30}ClF_3N_2O_2S$; molecular weight = 503.02; Calculated: %C, 57.30; %H, 6.01; %N, 5.57; %S, 6.37; %Cl, 7.05; Found: %C, 57.3; %H, 6.2; %N, 5.4; %S, 6.4; %Cl, 6.8.

I.R. Spectrum (chloroform) Presence of NH at 2550 cm$^{-1}$, of OH at 3350 cm$^{-1}$ U.V. Spectrum (ethanol) Max. at 307 nm; ε = 3520; Max. at 257.5 nm; ε = 32750.

EXAMPLE XLVIII 10.8 g of 2-trifluoromethyl-10-[3-(4-β-hydroxyethoxy-4-methylpiperidino)-propyl]-phenothiazine (prepared as in Example XLVII) were dissolved in 100 ml of anhydrous benzene containing 4.2 ml of triethylamine. The obtained solution was cooled to +5° C and a solution of 4.45 g of heptanoic acid chloride in 50 ml of anhydrous benzene was added dropwise over 30 minutes. The mixture was stirred for 24 hours at room temperature and the precipitate formed was removed by filtration and the benzene filtrate was washed with a 5% aqueous solution of sodium bicarbonate, then with water. After drying and evaporation of the benzene solution to dryness, 12.5 g of a crude oily product were obtained which was purified by chromatography on silica gel. The product was eluted with ethanol to obtain 10 g of a product which was treated with active charcoal. After filtration and removal of the solvent, 6.5 g of 2-trifluoromethyl-10-[3-(4-$\beta$-heptanoyloxyethyl-4-methylpiperidino)-propyl]-phenothiazine were obtained as a yellow oil soluble in ether and ethanol and slightly soluble in water.

Analysis: $C_{31}H_{41}F_3N_2O_3S$; molecular weight = 578.73; Calculated: %C, 64.33; %H, 7.14; %F, 9.85; %N, 4.84; %S, 5.54; Found: %C, 64.3; %H, 7.2; %F, 9.9; %N, 4.5; %S, 5.3.

EXAMPLE XLIX 37.7 g of 10-(3-chloropropyl)-2-trifluoromethyl-phenothiazine were dissolved in 100 ml of methyl ethyl ketone and 16.5 g of sodium iodide, 11.1 g of triethylamine and then 19 g of 2-(4-ethyl-4-piperidyloxy)-ethanol dissolved in 100 ml of methyl ethyl ketone were successively added thereto. The mixture was refluxed for 20 hours and after cooling, the precipitate formed was removed by vacuum filtration. The filtrate was evaporated to dryness and the residue was dissolved in methylene chloride. The organic solution was washed with an aqueous solution of sodium bicarbonate, then with water, dried and concentrated to dryness. The residue was dissolved in an ethanol-ether mixture to which was added an ether solution of hydrogen chloride. The precipitate formed was recovered by vacuum filtration and was crystallized from isopropanol, then from acetonitrile to obtain 27 g of 2-trifluoromethyl-10-[3-(4-$\beta$-hydroxyethoxy-4-ethyl-piperidino)-propyl]-phenothiazine hydrochloride as white crystals, melting at 204° C and soluble in chloroform, water, dilute hydrochloride acid and methylene chloride.

Anaylsis: $C_{25}H_{32}ClF_3N_2O_2S$; molecular weight = 517.07; Calculated: %C, 58.08; %H, 6.20; %N, 5.42; %F, 11.04; %N, 6.87; %Cl, 6.21; Found: %C, 57.9; %H, 6.4; %N, 5.5; %F, 11.1; %N, 7.1; %Cl, 6.4.

I.R. Spectrum (chloroform) Presence of OH at 3610 $cm^{-1}$, of $NH^+$;

U.V. Spectrum (ethanol) Max. at 259 nm, $\epsilon$ = 32 200; Max. at 306 nm; $\epsilon$ = 7 500.

EXAMPLE L 10 g of 2-trifluoromethyl-10-(3-chloropropyl)-phenothiazine were dissolved in 50 ml of methyl ethyl ketone and 4.36 g of sodium iodide, 2.9 g of triethylamine, then dropwise a solution of 5.4 g of 2-(4-propyl-4-piperidyloxy)-ethanol in 50 ml of methyl ethyl ketone were added successively thereto. The mixture was refluxed for 24 hours and after cooling, the precipitate formed was removed by vacuum filtration. The precipitate formed was removed by filtration and the filtrate was evaporated in vacuo and the residue was dissolved in methylene chloride. The organic solution was washed with an aqueous solution of sodium bicarbonate, then with water and the solution was dried and concentrated in vacuo to obtain 14.2 g of 2-trifluoromethyl-10-[3-(4-$\beta$-hydroxyethoxy-4-propyl-piperidino)-propyl]-phenothiazine as a beige product which was dissolved in 50 ml of ethanol. The resulting solution was reacted with an ether solution of hydrogen chloride and the hydrochloride was precipitated by the addition of ether. The said precipitate was recovered by vacuum filtration and was washed with ether and crystallized from acetonitrile to obtain 7 g of 2-trifluoromethyl-10-[3-(4-$\beta$-hydroxyethoxy-4-propyl-piperidino)-propyl]-phenothiazine hydrochloride as white crystals melting at 192° C.

Analysis: $C_{26}H_{34}F_3ClN_2O_2S$; molecular weight = 531.08; Calculated: %C, 58.80; %H, 6.45; %F, 10.73; %Cl, 6.68; %N, 5.27; %S, 6.04; Found: %C, 58.9; %H, 6.4; %F, 11.1; %Cl, 6.9; %N, 5.0; %S, 6.0.

I.R. Spectrum (chloroform) Presence of $NH^+$ and of OH, free and associated

U. V. Spectrum (ethanol) Max. at 259 nm; $\epsilon$ = 33,200 Max. at 309 nm; $\epsilon$ = 3,560

EXAMPLE LI 14.1 g of 2-trifluoromethyl-10-(3-chloropropyl)-phenothiazine were dissolved in 50 ml of methyl ethyl ketone and 6.14 g of sodium iodide, 4.15 g of triethylamine, then 10 g of 2-(4-heptyl-4-piperidyloxy)-ethanol dissolved in 50 ml of methyl ethyl ketone were successively added thereto. The mixture was refluxed with agitation for 40 hours and after cooling, the precipitate formed was removed by vacuum filtration. The organic solution was washed with an aqueous solution of sodium bicarbonate, then with water, dried and then concentrated. The said product was reacted with an ether solution of hydrogen chloride and the obtained precipitate was recovered by vacuum filtration and was crystallized from an ethanol ether mixture to obtain 7.8 g of 2-trifluoromethyl-10-[3-(4-heptyl-4-$\beta$-hydroxyethoxy-piperidino)-$\beta$-propyl]-phenothiazine hydrochloride as white crystals melting at 180° C and soluble in ethanol and insoluble in water and ether.

Analysis: $C_{30}H_{42}ClF_3N_2SO_2$; molecular weight = 587.17; Calculated: %C, 61.36; %H, 7.21; %Cl, 6.04; %N, 4.77; %F, 9.71; Found: %C, 61.1; %H, 7.0; %Cl, 6.2; %N, 4.5; %F, 9.7.

I.R. Spectrum (chloroform) Presence of $NH^+$ at 2600 $cm^{-1}$, of OH at 3310 $cm^{-1}$ and of $—CF_3$ at 1320 to 1340 $cm^{-1}$ and at 1118 to 1165 $cm^{-1}$.

EXAMPLE LII 5.5 g of 2-trifluoromethyl-10-[3-(4-heptyl-4-$\beta$-hydroxyethoxy-piperidino)-propyl]-phenothiazine, prepared in Example LI, were dissolved in 30 ml of anhydrous benzene containing 1.17 g of triethylamine and a solution of 1.21 g of propionyl chloride in 20 ml of anhydrous benzene was added thereto dropwise. The mixture was agitated during 50 hours at rrom temperature and the precipitate formed was removed by filtration. The benzene filtrate was washed with an aqueous solution of sodium bicarbonate, then with water, dried and concentrated to obtain 5.1 g of crude oily product which was purified by precipitation as its acidic oxalate by the addition of oxalic acid. The precipitate was vacuum filtered and crystallized from an ethanol-ether mixture to obtain 3.15 g of the acid oxalate of 2-trifluoromethyl-10-[3-(4-heptyl-4-$\beta$-propionyloxyethoxy-piperidino)-propyl]-phenothiazine. The precipitate was suspended in anhydrous ether and a current of ammonia was bubbled therethrough. After removal of the formed ammonium oxalate by filtration and evaporation of ether, 2.4 g of 2-trifluoromethyl-10-[3-(4-heptyl-4-β-propionyloxyethoxy-piperidino)-propyl]-phenothiazine were obtained as a colorless oil.

Analysis: $C_{33}H_{45}F_3N_2O_3S$; molecular weight = 606.77; Calculated: %C, 65.30; %H, 7.48; %F, 9.4; %N, 4.62; %S, 5.3; Found: %C, 65.0; %H, 7.4; %F, 9.7; %N, 4.8; %S, 5.3.

I.R. Spectrum (chloroform) Presence of C=O ester at 1734 cm$^{-1}$, of C=C characteristic of phenothiazines at 1568 and 1600 cm$^{-1}$ and of —CF$_3$ from 1322 to 1355 cm$^{-1}$ and from 1122 to 1165 cm$^{-1}$.

EXAMPLE LIII 2-trifluoromethyl-10-[3-(4-{2-decanolyloxyethoxy}-4-methyl-piperidino)-propyl]-phenothiazine STEP A: 2-trifluoromethyl-10-[3-(4-{2-hydroxyethoxy}-4-methyl-piperidino)-propyl]-phenothiazine 8.12 g of sodium iodide and 5.5 g of triethylamine and then a solution of 8.7 g of 2-(4-methyl-4-piperidyl)-oxyethanol in 50 ml of methyl ethyl ketone were added to a solution of 18.7 g of 2-trifluoromethyl-10-(3-chloropropyl)-phenothiazine in 50 ml of methyl ethyl ketone and the mixture was refluxed for 20 hours and then was cooled. The solid phase was removed by vacuum filtration and the filtrate was evaporated under reduced pressure. The residue was taken up in methylene chloride and the organic solution was washed with aqueous sodium bicarbonate solution and then with water, dried and concentrated to dryness under reduced pressure to obtain 20 g of 2-trifluoromethyl-10-[3-(4-{2-hydroxyethoxy}-4-methyl-piperidino)-propyl]-phenothiazine which was used as is for the next step.

STEP B: 2-trifluoromethyl-10-[3-(4-{2-decanolyoxyethoxy}-4-methyl-piperidino)-propyl]-phenothiazine 9.3 g of the product of Step A were dissolved in 50 ml of anhydrous benzene containing 2.2 g of triethylamine and after cooling the solution to 10° C, a solution of 4.2 g of decanoyl acid chloride in 20 ml of anhydrous benzene were added thereto dropwise. The mixture was stirred at room temperature for 20 hours and was then washed with water. The mixture was then stirred for 4 hours with 100 ml of an aqueousسodium bicarbonate saturated solution and the organic phase was decanted and concentrated to obtain 11.6 gm of a raw oily product. The product was purified by chromatography over silica gel and elution with 99-1 cyclohexane-triethylamine mixture. The eluant was evaporated to obtain 7 g of 2-trifluoromethyl-10-[3-(4-{2-decanoyloxyethoxy}-4-methyl-piperidino)-propyl]-phenothiazine in the form of a yellow oil.

Analysis: $C_{34}H_{47}F_3N_2O_3S$; molecular weight = 620.85; Calculated: %C, 65.78; %H, 7.63; %F, 9.18; %N, 4.51; %S, 5.17; Found: %C, 66.0; %H, 7.7; %F, 9.3; %N, 4.4; %S, 5.3.

EXAMPLE LIV 2-trifluoromethyl-10-[3-(4-{2-methyl-2-heptanoyloxyethoxy}-4-methyl-piperidino)-propyl]-phenothiazine A solution of 2.7 g of 2-methylheptanoic acid chloride in 10ml of anhydrous benzene was added dropwise at 10° C to a solution of 6.05 g of 2-trifluoromethyl-10-[3-(4-{2-hydroxyethoxy}-4-methyl-piperidino)-propyl]-phenothiazine in 50 ml of anhydrous benzene containing 1.7 g of triethylamine and the mixture was stirred at room temperature for 20 hours. After washing the benzene solution with water, the mixture was stirred for 4 hours with an aqueous solution saturated with sodium bicarbonate and the organic phase was decanted and concentrated.. The oily residue was purified by chromatography over silica gel with a 99-1 cyclohexane-triethylamine mixture as eluant to obtain 6.5 g of 2-trifluoromethyl-10-[3-(4-{2-methyl-2-heptanoyloxyethoxy}-4-methyl-piperidino)-propyl]-phenothiazine in the form of a yellow oil.

Analysis: $C_{32}H_{43}F_3N_2O_3S$; molecular weight = 592.78; Calculated: %C, 64.84; %H, 7.31; %N, 4.73; %F, 9.61; %S, 5.41; Found: %C, 65.1; %H, 7.5; %N, 4.5; %F, 9.7; %S, 5.3.

EXAMPLE LV 2-trifluoromethyl-10-[3-(4-{2-hexadecanoyloxyethoxy}-4-methylpiperidino)-propyl]-phenothiazine A solution of 3.3 g of hexadecanoic acid chloride in 20 ml of anhydrous benzene was added dropwise at 10° C to a solution of 5 g of 2-trifluoromethyl-10-[3-(4-{2-hydroxyethoxy}-4-methyl-piperidino)-propyl]-phenothiazine in 50 ml of anhydrous benzene containing 1.2 g of triethylamine and the mixture was stirred for 20 hours at room temperature. The mixture was washed with water and then was stirred for 4 hours with 100 ml of an aqueous saturated sodium bicarbonate solution. The organic phase was decanted and concentrated. The oily residue was subjected to chromatography over silica gel with a 98-2 benzene-triethylamine mixture as eluant to obtain 6.4 g of 2-trifluoromethyl-10-[3-(4-{2-hexadecanoyloxyethoxy}-4-methyl-piperidino)-propyl]-phenothiazine in the form of a yellow oil.

Analysis: $C_{40}H_{59}F_3N_2O_3S$; molecular weight = 705.02; Calculated: %C, 68.15; %H, 8.44; %F, 8.08; %N, 3.97; %S, 4.55; Found: %C, 67.8; %H, 8.7; %F, 8.2; %N, 3.6; %S, 4.8.

EXAMPLE LVI

Acid Maleate of 2-trifluoromethyl-10-[3-(4-{2-hydroxyethoxy}-4-ethyl-piperidino)-propyl]-phenothiazine A solution of 1.10 g of maleic acid in 50 ml of ethyl acetate was added with stirring at room temperature to a solution of 4.8 g of 2-trifluoromethyl-10-[3-(4-{2-hydroxyethoxy}-4-ethyl-piperidino)-propyl]-phenothiazine in 50 ml of ethyl acetate and after adding 200 ml of anhydrous ether, the mixture was allowed to stand for 3 days. The precipitate formed was recovered an washed with ether to obtain, after drying, 4.6g of acid maleate of 2-trifluoromethyl-10-[3-(4-{2-hydroxyethoxy}-4-ethyl-piperidino)-propyl]-phenothiazine as white crystals melting at 95° C.

Analysis: $C_{29}H_{35}F_3N_2O_6S$; molecular weight = 596.68; Calculated: %C, 58.28; %H, 5.91; %F, 9.55; %N, 4.70; %S, 5.37; Found: %C, 58.0; %H, 5.9; %F, 9.9; %N, 4.4; %S, 5.5.

EXAMPLE LVII 2-trifluoromethyl-10-[3-(4-{2-decanoyloxyethoxy}-4-ethylpiperidino)-propyl]-phenothiazine A solution of 3.5 g of decanoic acid chloride in 20 ml of anhydrous benzene was added dropwise at 10° C to a solution of 7.2 g of 2:trifluoromethyl-10-[3-(4-{2-hydroxyethoxy}-4-ethyl-piperidino)-propyl]-phenothiazine in 100 ml of anhydrous benzene containing 2 g of triethylamine and the mixture was stirred at room temperature for 24 hours. The benzene phase was washed with an aqueous saturated sodium bicarbonate solution, then with water, dried over magnesium sulfate and the benzene was evaporated under reduced pressure. The oily residue was purified by chromatography over silica gel with ethanol as eluant to obtain 4 g of 2-trifluoromethyl-10-[3-(4-{2-decanoyloxyethoxy}-4-ethyl-piperidino)-propyl]-phenothiazine in the form of a yellow oil.

Analysis: $C_{35}H_{49}N_2F_3O_3S$; molecular weight = 634.86; Calculated: %C, 66.22; %H, 7.78; %F, 8.98; %N, 4.41; %S, 5.05; Found: %C, 66.1; %H, 7.9; %F, 8.7; %N, 4.6; %S, 5.3.

PHARMACEUTICAL EXAMPLES

A. TABLETS

Tablets weighing 250 mg were prepared from an excipient consisting of lactose, starch, talc and magnesium stearate and 25 mg of the acid succinate of 2-trifluoromethyl-10-[3-(4-β-hydroxyethoxy-piperidino)-propyl]-phenothiazine.

Tablets weighing 250 mg were prepared from an excipient consisting of lactose, starch, talc and magnesium stearate and 25 mg of 10-[3-(4-β-hydroxyethoxy-piperidino)-propyl]-phenothiazine hydrochloride.

Tablets weighing 250 mg were prepared from an excipient consisting of lactose, starch, talc and magnesium stearate and 25 mg of 2-trifluoromethyl-10-[3-(4-{4-acetoxybutoxy}-piperidino)-propyl]-phenothiazine.

Tablets weighing 250 mg were prepared from an excipient consisting of talc, starch, lactose and magnesium stearate and 25 mg of the acid oxalate of 2-trifluoromethyl-10-[3-(4-β-heptyloxycarbonyloxyethoxy-piperidino)-propyl]-phenothiazine.

Tablets weighing 200 mg were prepared from 180 mg of excipient consisting of lactose, amidon, talc and magnesium stearate and 20 mg of 2-trifluoromethyl-10-[3-(4-β-hydroxyethoxy-4-methyl-piperidino)-propyl]-phenothiazine hydrochloride.

Tablets weighing 200 mg were prepared from 175 mg of an excipient consisting of talc, amidon and magnesium stearate and 25 mg of acid maleate of 2-trifluoromethyl-10-[3-(4-{2-hydroxyethoxy}-4-ethyl-piperidino)-propyl]-phenothiazine.

B. INJECTABLE SOLUTIONS

Injectable solutions were prepared by adding sufficient sesame oil to 25 mg of either 2-trifluoromethyl-10-[3-(4-{2-heptanoyloxyethoxy}-4-methyl-piperidino)-propyl]-phenothiazine or 2-trifluoromethyl-10-[3-(4-{2-decanoyloxyethoxy}-4-ethyl-piperidino)-propyl]-phenothiazine to make a total volume of 1 ml.

C. OINTMENT

An ointment was prepared from 98 g of an excipient and 2 g of the acid succinate of 2-trifluoromethyl-10-[3-(4-β-hydroxyethoxy-piperidino)-propyl]-phenothiazine hydrochloride.

PHARMACOLOGICAL STUDY

A. Neuroleptic Activity

The neuroleptic activity of the products were investigated by the following 4 tests:

1. The traction test which consists of suspending a mouse by the front paws and presenting to him a metallic thread stretched horizontally. In less than 5 seconds, the normal animal effects a restoration by putting at least one of his hind paws on the thread. This test is carried out 25 minutes after administration of the test product. The $DE_{50}$ dose, the dose which prevents 50% of the animals from effecting the restoration in less than 5 seconds, was determined.
2. The chimney test which consists in placing a mouse at the end of a glass tube 30 cm in length, whose diameter is adapted to the tail of the animal. After the tube is erected vertically with a quick gesture, the animal with head down normally remounts the whole length of the tube in less than 30 seconds. This test is carried out 25 minutes after administration of the test product. The $DE_{50}$, the dose which prevents 50% of the animals to effect the remounting in less than 30 seconds, was determined;
3. The test of cataleptic activity by the technique described by BOISSER et al [Therapie, (1963), Vol. 18, p 1257 – 1277]. The test was conducted on young rats and consists in crossing the homolateral paws and noting the intensity of the catalepsy. The $DE_{50}$, the dose which causes a catalepsy in 50% of the animals after administration of the product, was determined;
4. The anti-emetic activity test which has been investigated in dogs with a subcutaneous injection of 0.1 mg/kg of apormorphine hydrochloride. The $DE_{50}$, the dose which reduces 50% of the numbers of vomiting caused by the injection of 0.1 mg/kg of apomorphine chlorohydrate, was determined.

The results obtained by the 4 test listed above are given in Table I.

TABLE I

| Product described in example | Traction test $DE_{50}$ mg/kg i.p. | Chimney test $DE_{50}$ mg/kg i.p. | Cataleptic activity $DE_{50}$ mg/kg i.p. | Anti-emetic activity $DE_{50}$ mg/kg s.c. |
|---|---|---|---|---|
| XIII | 0.75 | 0.65 | 1.3 | 0.012 |
| XI | 10.5 | 10 | >40 | 0.060 |
| XV | 0.6 | 0.65 | 4 | 0.025 |
| XIV | 0.6 | 0.4 | 0.95 | 0.013 |
| XXX | 50 | 12.5 | 3.2 | — |
| XVI | 1.4 | 1.5 | 2.3 | 0.072 |
| XVII | 1.6 | 1.6 | 1.8 | 0.030 |
| XVIII | 0.5 | 0.5 | 3 | 0.035 |
| XX | 2 | 1.9 | 8 | 0.055 |
| XLVII | 0.85 | 0.55 | 1 | 0.0035 |

The results show the very interesting neuroleptic activity of the tested products.

In addition, proofs of antipsychotic activity have been obtained with the product of Example XIV. This activity is shown by conducting the test of stereotypes with apomorphine. The stereotype movements of the buccal sphere of rats after intravenous injection of 1.5 mg/kg of apomorphine hydrochloride are evaluated by the code indicated by JANSSEN et al. [Arzneim. Forsch., Vol 10, (1960), p 1003–1005]. Thus the $DE_{50}$, the dose which reduces by 50% after 15 minutes at the intensity of stereotypes due to injection of apormorphine hydrochloride, was determined for the product of Example XIV to be 0.5 mg/kg intraperitoneally.

A test of toxicity of the amphetamine groups was also conducted on lots of 10 male mice grouped in a space of limited dimensions. A dose of 15 mg/kg of dexamphetamine sulfate was injected intraperitoneally after the administration of the product of Example XIV. Thus, the $DE_{50}$ dose, the dose which protects the animals after 24 hours, was determined for the product of Example XIV to be 0.07 mg/kg intraperitoneally. Thus, this product is endowed with a particularly intense anti-psychotic activity.

the administration. The obtained results are in Table III.

TABLE III

| Tested products of Examples | XIII | XI | XV | XIV | XXX | XVI | XVII | XVIII | XIX | XX | XXI | XXII | XLVII |
|---|---|---|---|---|---|---|---|---|---|---|---|---|---|
| DL$_{50}$ mg/kg i.p. | 95 | 130 | 95 | 160 | >1600 | 155 | 138 | 120 | 115 | 140 | 195 | 170 | 150 |

B. Antagonistic Activity towards Histamine and Acetylchloine:

The activity of the products was determined on the isolated ileum of the guinea pig by the technique of Magnus [Arch. Ges. Physiol., Vol. 102, (1904), p. 123], against the contracturing action of histamine and acetylcholine. The duration of contact of the product before the addition to the histamine or acetylcholine bath at a sub-maximum dose, was set at 30 seconds. The CE$_{50}$, the concentration which brings about a 50% inhibition of the contraction of the ileum, was determined.

Most of the investigated products show a considerable anti-histaminic activity. For example, the products of the Examples XIII, XIV, XVI, XVIII, XIX, XX, XXI and XXII inhibit the contracturing action caused by histamine at concentrations between $10^{-8}$ and $10^{-7}$ gm/l and the products of the Examples XI and XV were active at concentrations below $10^{-9}$ gm/l. Likewise, these products as well as the product of Example XLVII are active against the contracturing action caused by acetylcholine at concentrations from $10^{-6}$ to $10^{-5}$ gm/l.

C. Analgesic Activity

The analgesic activity was investigated in mice by the hot plate method of EDDY. For each compound, the administered dose (intraperitoneally) in mg/kg and the percentage of animals whose reaction time was above 45 seconds (TR>45 seconds). is indicated in Table II. The analgesic activity was also investigated in mice by the phenylbenzoquinone test according to SIEGMUND et al. [Proc. Soc. Exper. Biol. Med., Vol. 95, (1957), p. 729.]. This analgesic activity was evaluated by establishing the DE$_{50}$ of the compounds which is the dose which reduces the number of stretchings by 50%. Results are in Table II.

TABLE II

| Product described in example | Eddy Test | | Phenylbenzoquinone test DE$_{50}$ in mg/kg p.o. |
|---|---|---|---|
| | Dose in mg/kg i.p. | % of animals whose TR>45 s | |
| XIII | 12.5 | 100 | 2.5 |
| XV | 12.5 | 100 | 2.8 |
| XIV | 25 | 100 | 2.0 |
| XXX | 200 | 100 | 7.0 |
| XVI | 50 | 100 | 1.5 |
| XVII | 25 | 90 | 1.0 |
| XVIII | 25 | 100 | 0.25 |
| XIX | 12.5 | 80 | 3.8 |
| XX | 25 | 100 | 0.55 |
| XLVII | | | 1.2 |

These results show the analgesic activity of the tested products.

D. Acute Toxicity:

The 50% lethal doses (DL$_{50}$) of different test products were evaluated after intraperitoneal administration in mice. The mortality was recorded 48 hours after

E. Retarded Neuroleptic Activity:

The test for toxicity of the amphetamine group was selected to show the retarded neuroleptic activity of the products. This retarded activity was compared to that of the product of Example XIV with the above test to show the antipsychotic activity. A dose of 20 mg/kg of dexamphetamine sulfate was injected intraperitoneally 1 to 3 days after the subcutaneous injection of the test product in solution in sesame oil. The mortality was counted summarily 24 hours after the injection of the dexamphetamine. The obtained results are shown in the Table IV.

TABLE IV

| Tested products of examples | Dose mg/kg S.C. | Percentage of mortality (24 hours) after | |
|---|---|---|---|
| | | 1 day | 3 days |
| XIV | 10 | 0 | 60 |
| | 20 | 0 | 60 |
| XXXVII | 10 | 0 | 0 |
| | 20 | 0 | 0 |
| XXXIV | 10 | 40 | 10 |
| | 20 | 0 | 0 |
| XXXII | 10 | 0 | 0 |
| | 20 | 0 | 0 |
| XXVII | 10 | 0 | 20 |
| | 20 | 0 | 0 |
| XLI | 10 | 0 | 0 |
| | 20 | 0 | 0 |
| XXIX | 10 | 0 | 50 |
| | 20 | 0 | 0 |
| XLIII | 10 | 0 | 50 |
| | 20 | 0 | 0 |
| XLIV | 10 | 0 | 60 |
| | 20 | 0 | 0 |
| XLV | 10 | 0 | 20 |
| | 20 | 0 | 0 |

F. Neuroleptic Activity

The duration of the neuroleptic activity of the compounds of Examples XLVIII, LIII, LIV, LV and LVII were compared by the test of toxicity of amphetaminic group, test of stereotypes provoked by amphetamine and anti-emetic activity as discussed below and the results are reported in Table V.

1. Antagonism to amphetaminic group toxicity

This antagonism was determined on groups of 10 male mice gathered in a crystallizer with a 20 cm diameter and 9 cm in height closed with a grilled lid. After subcutaneous injection of 20 mg/kg of the test product in solution in sesame oil, group of mice at variable times received a single intraperitoneal injection of dexamphetamine sulfate. These latter injections were made 1, 2 or 4 hours or 1, 3, 7, 14 or 21 days after administration of the test product. The morality for each group was determined 24 hours after the administration of dexamphetamine sulfate. The time in days was determined for the antagonism of the test product to toxicity of amphetamine as manifested by an average of 50% of the animals.

2. Antagonism with regard to stereotypes provoked by amphetamine

This antagonism was determined on groups of 5 rats with each animal being individually placed in a grilled cage. After a subcutaneous injection of 20 mg/kg of the test product in solution in sesame oil, each animal of a group received intraperitoneally a single dose of 8 gm/kg of dexamphetamine sulfate either ½ hour or 1, 3, 7 or 14 days thereafter. Each test included a group of treated animals and a group of control animals. The rating scale adopted is that set forth by Halliwel et al [Brit. J. Pharmacol., Vol. 23 (1964), p. 330–350] and the sum of the scores was calculated for each control group and each treated group. The duration in days in which the score of the treated animals diminished by 50% in comparison to the control animals is reported in Table V.

3. Anti-emetic activity

The antagonism with regard to the emetic activity of apomorphine was studied on groups of 3 or 4 dogs. 8 days before the start of the test, the number of vomiting provoked by a single subcutaneous injection or apomorphine hydrochloride was determined for each animal. After subcutaneous injection of 0.3 mg/kg of the test product in solution in sesame oil, each animal of a group received subcutaneously a dose of 0.1 kg/mg of apomorphine hydrochloride ½ hour or 7, 14 or 21 days thereafter. The duration in days during which the anti-emetic activity of the test products reduced by 50% the number of vomitings provoked by injection of 0.1 mg/kg of apomorphine hydrochloride is reported in Table V.

TABLE V

| Compound of Example | Test 1 | Test 2 | Test 3 |
|---|---|---|---|
| XLVIII | 17 days | 7 days | 15 days |
| LIII | 6 days | 5 days | — |
| LIV | 5 days | 5.5 days | — |
| LV | 3 days | 4 days | 25 days |
| LVII | 3 days | 3 days | 14 days |

The results of Table V shows that the tested products possess a very important prolonged neuroleptic activity.

Varius modifications of the products and method of the invention may be made without departing from the spirit or scope thereof and it is to be understood that the invention is to be limited only as defined in the appended claims.

We claim:

1. A compound of the formula

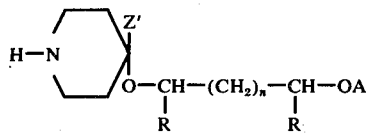

wherein R is selected from the group consisting of hydrogen and alkyl of 1 to 4 carbon atoms, Z' is selected from the group consisting of hydrogen and alkyl of 1 to 10 carbon atoms, n is 0, 1 or 2 and A is selected from the group consisting of hydrogen, —COOR$_2$ and —COR$_1$, R$_2$ is linear alkyl of 1 to 15 carbon atoms and R$_1$ is selected from the group consisting of alkyl of 1 to 18 carbon atoms optionally substituted with a double bond or —O— and polymethoxyphenyl.

2. A 1-benzyl-4-piperidyloxy-alkanols of the formula

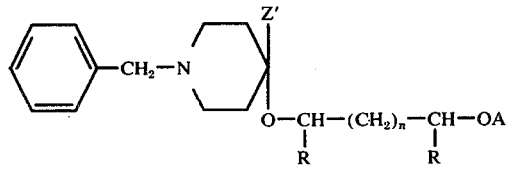

wherein R is selected from the group consisting of hydrogen and alkly of 1 to 4 carbon atoms, Z' is selected from the group consisting of hydrogen and alkyl of 1 to 10 carbon atoms, n is 0, 1 or 2 and A is selected from the group consisting of hydrogen, —COOR$_2$ and —COR$_1$, R$_2$ is linear alkyl of 1 to 15 carbon atoms and R$_1$ is selected from the group consisting of alkyl of 1 to 18 carbon atoms optionally substituted with a double bond or —O— and polymethoxyphenyl.

3. A process for the preparation of a compound of claim 1 which comprises reacting a cyclic acetal of 1-benzyl-4-piperidone of the formula

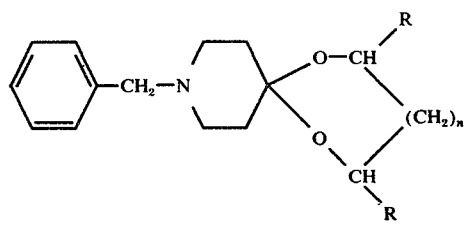

with lithium aluminum hydride in the presence of a Lewis acid or an organo magnesium compound of the formula $$Z-Mg-Hal$$

wherein Hal is chlorine, bromine or iodine and Z is alkyl of 1 to 10 carbon atoms to obtain the corresponding compound of the formula

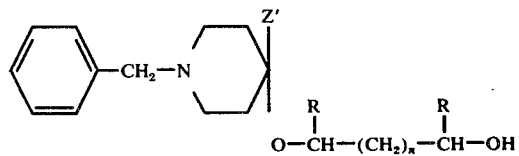

wherein R, Z' and n have the above definition, reacting the latter with hydrogen in the presence of a palladium catalyst to form the corresponding compound of claim 1.

4. A neuroleptic composition comprising an effective amount of a compound of the formula

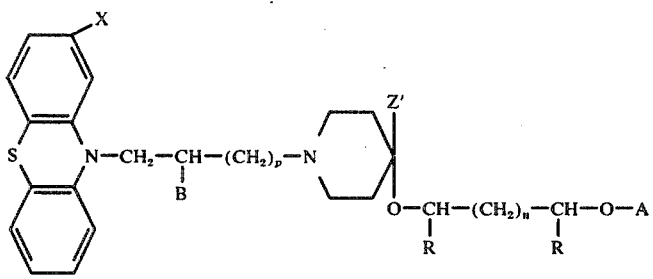

wherein X is selected from the group consisting of hydrogen, chlorine, —CF$_3$, —OCH$_3$ and SCH$_3$, B and R are individually selected from the group consisting of hydrogen and alkyl of 1 to 4 carbon atoms, Z' is selected from the group consisting of hydrogen and alkyl of 1 to 10 carbon atoms, p is 0 or 1, n is 0, 1 or 2 and A is selected from the group consisting of hydrogen, —COOR$_2$ and —COR$_1$, R$_2$ is linear alkyl of 1 to 15 carbon atoms and R$_1$ is selected from the group consisting of alkyl of 1 to 18 carbon atoms optionally containing a double bond or —O— and a polymethoxyphenyl and their non-toxic, pharmaceutically acceptable acid addition salts and an inert pharmaceutical carrier.

5. A method of treating maniac excitation in warm-blooded animals which comprises administering to warm-blooded animals an effective amount of a compound of the formula

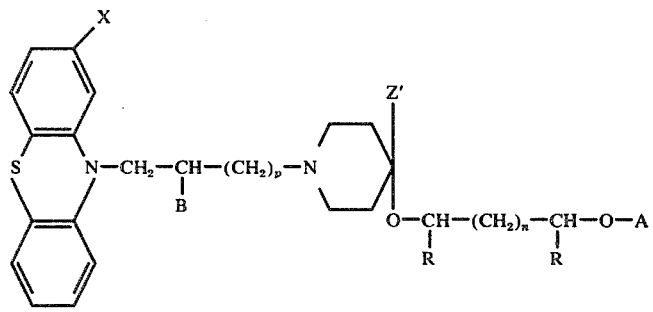

wherein X is selected from the group consisting of hydrogen, chlorine, —CF$_3$, —OCH$_3$ and SCH$_3$, B and R are individually selected from the group consisting of hydrogen and alkyl of 1 to 4 carbon atoms, Z' is selected from the group consisting of hydrogen and alkyl of 1 to 10 carbon atoms, p is 0 or 1, n is 0,1 or 2 and A is selected from the group consisting of hydrogen, —COOR$_2$ and —COR$_1$, R$_2$ is linear alkyl of 1 to 15 carbon atoms and R$_1$ is selected from the group consisting of alkyl of 1 to 18 carbon atoms optionally containing a double bond or —O— and a polymethoxyphenyl and their non-toxic, pharmaceutically acceptable acid addition salts.

6. The method of claim 5 wherein the compound is selected from the group consisting of 10-[3-(4-$\beta$-hydroxyethoxy-piperidino)-propyl]-2-trifluoromethyl-phenothiazine and its nontoxic, pharmaceutically acceptable acid addition salts.

7. The method of claim 5 wherein the compound is selected from the group consisting of 10-{3-[4-(2-hexadecanoyloxyethoxy)-piperidino]-propyl}-2-trifluoromethyl-phenothiazine and its nontoxic, pharmaceutically acceptable acid addition salts.

8. The method of claim 5 wherein the compound is selected from the group consisting of 10-[2-methyl-3-(4-$\beta$-hydroxyethoxypiperidino)-propyl]-2-methoxy-phenothiazine and its nontoxic, pharmaceutically acceptable acid addition salts.

* * * * *